United States Patent
Hay et al.

(10) Patent No.: US 10,183,055 B2
(45) Date of Patent: *Jan. 22, 2019

(54) ANG-(1-7) DERIVATIVE OLIGOPEPTIDES FOR THE TREATMENT OF PAIN AND OTHER INDICATIONS

(71) Applicant: ARIZONA BOARD OF REGENTS ON BEHALF OF THE UNIVERSITY OF ARIZONA, Tucson, AZ (US)

(72) Inventors: Meredith Hay, Tucson, AZ (US); John Konhilas, Tucson, AZ (US); Robin L. Polt, Tucson, AZ (US); Todd Vanderah, Tucson, AZ (US); Brittany Forte, Tucson, AZ (US); Tally Milnes, Tucson, AZ (US); Evan Jones, Tucson, AZ (US); Lajos Szabo, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/401,944

(22) Filed: Jan. 9, 2017

(65) Prior Publication Data

US 2017/0304391 A1 Oct. 26, 2017
US 2018/0028596 A9 Feb. 1, 2018

Related U.S. Application Data

(63) Continuation-in-part of application No. 15/134,073, filed on Apr. 20, 2016, now Pat. No. 9,670,251, which is a continuation of application No. 14/801,557, filed on Jul. 16, 2015, now Pat. No. 9,796,759.

(60) Provisional application No. 62/027,219, filed on Jul. 21, 2014.

(51) Int. Cl.
*A61K 38/08* (2006.01)
*C07K 7/06* (2006.01)
*C07K 7/14* (2006.01)
*C07K 9/00* (2006.01)

(52) U.S. Cl.
CPC ........... *A61K 38/085* (2013.01); *C07K 7/06* (2013.01); *C07K 7/14* (2013.01); *C07K 9/001* (2013.01)

(58) Field of Classification Search
None
See application file for complete search history.

(56) References Cited

U.S. PATENT DOCUMENTS

| 5,629,292 A | 5/1997 | Rodgers et al. |
| 5,716,935 A | 2/1998 | Rodgers et al. |
| 5,834,432 A | 11/1998 | Rodgers et al. |
| 5,955,430 A | 9/1999 | Rodgers et al. |
| 6,096,709 A | 8/2000 | Rodgers et al. |
| 6,110,895 A | 8/2000 | Rodgers et al. |
| 6,165,978 A | 12/2000 | Rodgers et al. |
| 6,177,407 B1 | 1/2001 | Rodgers et al. |
| 6,239,109 B1 | 5/2001 | Rodgers et al. |
| 6,248,587 B1 | 6/2001 | Rodgers et al. |
| 6,258,778 B1 | 7/2001 | Rodgers et al. |
| 6,335,195 B1 | 1/2002 | Rodgers et al. |
| 6,444,646 B1 | 9/2002 | Rodgers et al. |
| 6,455,500 B1 | 9/2002 | Rodgers et al. |
| 6,455,501 B1 | 9/2002 | Rodgers et al. |
| 6,475,988 B1 | 11/2002 | Rodgers et al. |
| 6,482,800 B1 | 11/2002 | Rodgers et al. |
| 6,498,138 B1 | 12/2002 | Rodgers et al. |
| 6,566,335 B1 | 5/2003 | Rodgers et al. |
| 6,730,775 B1 | 5/2004 | Rodgers et al. |
| 6,747,008 B1 | 6/2004 | Rodgers et al. |
| 6,762,167 B1 | 7/2004 | Rodgers et al. |
| 6,821,953 B1 | 11/2004 | Rodgers et al. |
| 6,916,783 B2 | 7/2005 | Rodgers et al. |
| 7,022,675 B2 | 4/2006 | Rodgers et al. |
| 7,118,748 B1 | 10/2006 | Rodgers et al. |
| 7,122,523 B2 | 10/2006 | Rodgers et al. |
| 7,173,011 B2 | 2/2007 | Rodgers et al. |
| 7,176,183 B2 | 2/2007 | Rodgers et al. |
| 7,288,522 B1 | 10/2007 | Rodgers et al. |

(Continued)

FOREIGN PATENT DOCUMENTS

| JP | 2011-500677 A | 1/2011 |
| JP | 2013-047249 A | 3/2013 |

(Continued)

OTHER PUBLICATIONS

Medical News 2016 "Neuropathy:causes symptoms and treatments" accessed from medicalnewstoday.com on Apr. 12, 2017.*
Menon 2007 "Angiotensin1-7 inhibits growth of human lung adenocarcinoma xenografts in nude mice through a reduction in cyclooxygenase-2" Cancer Res 67:2809-2815.*
Smith 2013 "painful boney metastases" K J Pain 26(3):223-241.*
Sola 2010 "glycosylation of therapeutic proteins: an effective strategy to optimize efficacy" Biodrugs 24(1):9-21.*
Costa 2012 "Angiotensin-(1-7) induces peripheral antinociception through mas receptor activation in an opioid-independent pathway" Pharmacology 89(3-4):137-44.*

(Continued)

*Primary Examiner* — Adam Weidner
(74) *Attorney, Agent, or Firm* — Anthony C. Kuhlmann; One LLP

(57) ABSTRACT

The present invention provides oligopeptides, in particular, Ang-(1-7) derivatives, and methods for using and producing the same. In one particular embodiment, oligopeptides of the invention have higher blood-brain barrier penetration and/or in vivo half-life compared to the native Ang-(1-7), thereby allowing oligopeptides of the invention to be used in a wide variety of clinical applications including in treatment of cognitive dysfunction and/or impairment, pain, and traumatic brain injury.

21 Claims, 15 Drawing Sheets

Specification includes a Sequence Listing.

(56) References Cited

U.S. PATENT DOCUMENTS

| | | |
|---|---|---|
| 7,338,938 B2 | 3/2008 | Rodgers et al. |
| 7,744,927 B2 | 6/2010 | Rodgers et al. |
| 8,633,158 B1 | 1/2014 | Franklin |
| 8,969,310 B2 | 3/2015 | Beliveau et al. |
| 9,045,526 B2 | 6/2015 | Mosberg |
| 9,290,540 B2 | 3/2016 | De Vries et al. |
| 9,623,084 B2 | 4/2017 | Rodgers et al. |
| 9,688,724 B2 | 6/2017 | Rodgers et al. |
| 2002/0165141 A1 | 11/2002 | diZerega et al. |
| 2003/0203834 A1 | 10/2003 | Tallant et al. |
| 2004/0214272 A1 | 10/2004 | La Rosa et al. |
| 2005/0153890 A1 | 7/2005 | Pan et al. |
| 2008/0312129 A1 | 12/2008 | Souza Dos Santos et al. |
| 2009/0071397 A1 | 3/2009 | Yasuda et al. |
| 2009/0104210 A1 | 4/2009 | Tota et al. |
| 2009/0227507 A1 | 9/2009 | Rodgers et al. |
| 2010/0055146 A1 | 3/2010 | Haas et al. |
| 2011/0281805 A1* | 11/2011 | Walther ............. A61K 31/4178 514/21.7 |
| 2012/0129776 A1 | 5/2012 | Cohen et al. |
| 2013/0137637 A1 | 5/2013 | Cho et al. |
| 2013/0183683 A1 | 7/2013 | Pemberton et al. |
| 2013/0184208 A1 | 7/2013 | Alaoui-Ismaili et al. |
| 2013/0184212 A1 | 7/2013 | Camphausen et al. |
| 2013/0210726 A1 | 8/2013 | Franklin |
| 2014/0094497 A1 | 4/2014 | Franklin |
| 2014/0205631 A1 | 7/2014 | Larsen et al. |
| 2015/0057216 A1 | 2/2015 | Beringer et al. |
| 2016/0016996 A1 | 1/2016 | Hay et al. |
| 2016/0051622 A1 | 2/2016 | Rodgers et al. |
| 2016/0199436 A1 | 7/2016 | Sabharwal |

FOREIGN PATENT DOCUMENTS

| | | |
|---|---|---|
| WO | WO 02/06308 A2 | 1/2002 |
| WO | WO 2009/114461 A2 | 9/2009 |
| WO | WO 2012/021578 A1 | 2/2012 |
| WO | WO 2012/070936 A | 5/2012 |
| WO | WO 2013/090833 A1 | 6/2013 |
| WO | WO 2013/119870 A1 | 8/2013 |
| WO | WO 2013/172956 A1 | 11/2013 |
| WO | WO 2014/021942 A1 | 2/2014 |
| WO | WO 2014/055691 A1 | 4/2014 |
| WO | WO 2014/116587 A1 | 7/2014 |
| WO | WO 2014/151338 A1 | 9/2014 |
| WO | WO 2014/179440 A1 | 11/2014 |
| WO | WO 2015/189342 A1 | 12/2015 |
| WO | WO 2016/112247 A1 | 7/2016 |

OTHER PUBLICATIONS

Japanese Office Action, Application No. 2016-524300, dated Nov. 1, 2016.

Extended European Search Report, Application No. 14820282.3, dated Feb. 16, 2016.

Albrecht, "Angiotensin-(1-7)-induced plasticity changes in the lateral amygdala are mediated by COX-2 and NO", Learning and Memory, vol. 14, No. 3 (Mar. 2007) pp. 177-184.

Bodiga, et al., "Renin Angiotensin System in Cognitive Function and Dementia," Asian J. of Neurosci., vol. 19, No. 10 (2013) pp. 3952-3962.

Ciobica, et al., "Brain renin-angiotensin system in cognitive function: pre-clinical findings and implications for prevention and treatment of dementia", ACTA Neurol, Belg., vol. 109 (Jan. 2009) pp. 171-180.

Ciobica, et al., "The Effects of Angiotensin II and Angiotensin 1-7 in Cognitive Processes and Oxidative Stress in Rates, Relevance for Alzheimer's Disease", Alzheimer's & Dementia: The Journal of the Alzheimer's Association, vol. 7, No. 4 (Jul. 2011) pp. S112-S113.

Fontes, et al., "Evidence that angiotensin-(1-7) plays a role in central control of blood pressure at the ventro-lateral medulla acting through specific receptors," Brain Research, vol. 665 (Nov. 1994) pp. 175-180.

Hellner, et al., "Angiotensin-(1-7) enhances LTP in the hippocampus through the G-protein-coupled receptor Mas", Mol. Cell. Neurosci, vol. 29, No. 3 (Jul. 2005) pp. 427-435.

Jiang, et al., "ACE2-Ang-(1-7)-Mas Axis in Brain: A Potential Target for Prevention and Treatment of Ischemic Stroke," Current Neuropharmacology, (Jan. 2013) pp. 209-217.

Lazaroni, et al., "Angiotensin-(1-7)/Mas axis integrity is required for the expression of object recognition memory," Neurobiology of Learning & Memory, vol. 97, No. 1 (Oct. 2011) pp. 113-123, San Diego, CA, US.

Passos-Silva, et al., "Angiotensin-(1-7): beyond the cardio-renal actions," Clin. Sci., vol. 124, (2013) pp. 443-456, Great Britain.

Silva, et al., "Promising Neuroprotective Effects of the Angiotensin 1-7/ACE2/Mas axis in Stroke", Exp. Physiol. vol. 99, No. 2 (Feb. 2014) pp. 342-343.

Xie, et al., "Angiotensin-(1-7) improves cognitive function in rats with chronic cerebral hypoperfusion," Brain Research, vol. 1573 (May 2014) pp. 44-53.

Xu, et al., "ACE2/ANG-(1-7)/Mas pathway in the brain: the axis of good," Am. J. Physiol. Regul. Integr. Comp. Physiol., vol. 300 (Dec. 2010) pp. R804-R817.

WO, PCT/US15/40785 ISR and Written Opinion, dated Jan. 5, 2016.

Solá, et al., "Effects of Glycosylation on the Stability of Protein Pharmaceuticals", J. Pharm. Sci., vol. 98, No. 4 (2009) pp. 1223-1245.

EP, 15825041.5, Extended European Search Report, dated Dec. 22, 2017.

Ernould, "Substrate phosphorylation capacities of the major tyrosine protein kinase from the human promyelocytic cell line, HL-60", Int. J. Peptide Protein Res., 1994, vol. 43, pp. 496-504.

WO, PCT/US18/12893 ISR and Written Opinion, dated Jun. 20, 2018.

Jan Danser, A.H., et al., "The Angiotensin II Type 2 Receptor for Pain Control", Cell, 2014, pp. 1504-1506.

WO, PCT/US18/12893 Invitation to Pay Additonal Fees, dated Apr. 26, 2018.

GenBank Accession No. P01019, Annotation Updated on Mar. 28, 2018, pp. 1-11.

Walters, P.E., et al., "Angiotensin-(1-7) Acts as a Vasodepressor Agent via Angiotensin II Type 2 Receptors in Conscious Rats", Hypertension, 2005, vol. 45, pp. 960-966.

* cited by examiner

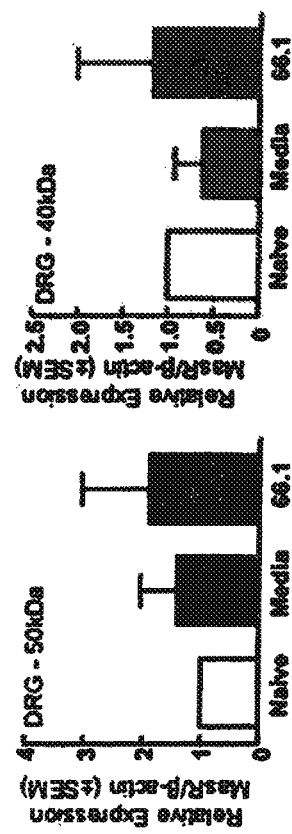
FIG. 11A
FIG. 11B
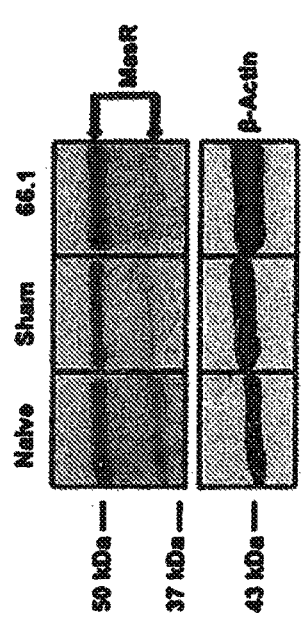
FIG. 11C
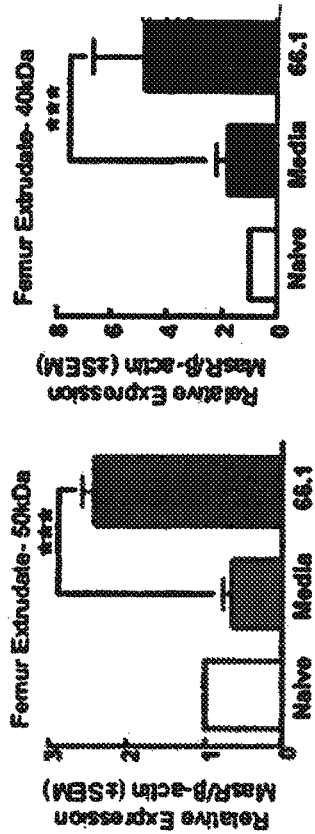
FIG. 11D

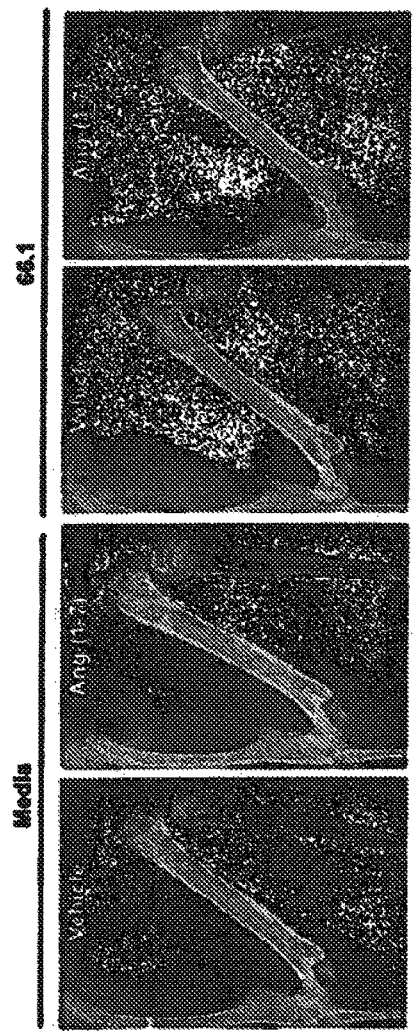
FIG. 13A
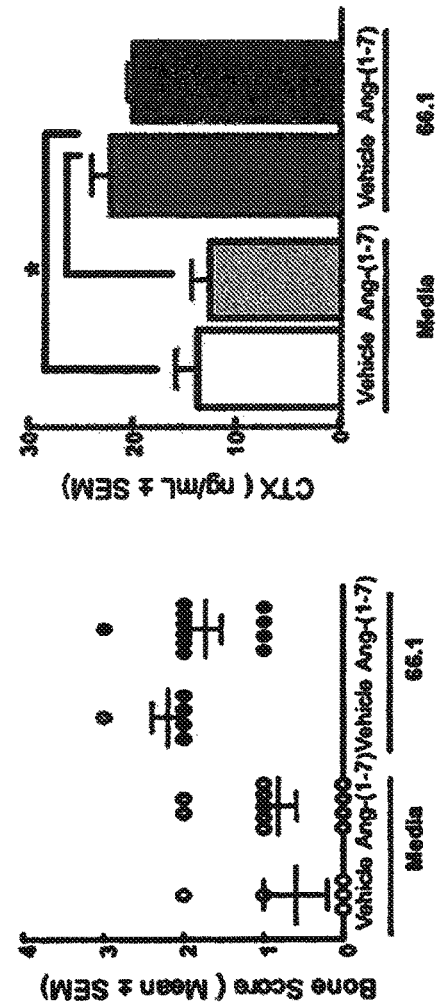
FIG. 13C
FIG. 13B

ANG-(1-7) DERIVATIVE OLIGOPEPTIDES FOR THE TREATMENT OF PAIN AND OTHER INDICATIONS

CROSS-REFERENCE TO RELATED APPLICATIONS

This application is a continuation-in-part of U.S. application Ser. No. 15/134,073, filed Apr. 20, 2016, which is a continuation of U.S. application Ser. No. 14/801,557, filed Jul. 16, 2015, which claims the priority benefit of U.S. Provisional Application No. 62/027,219, filed Jul. 21, 2014, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 2, 2017, is named 33032_4023_SL.txt and is 4,996 bytes in size.

FIELD OF THE INVENTION

The present invention relates to oligopeptides, such as Ang-(1-7) and related derivative oligopeptides and Mas receptor-binding non-peptides, and methods for using the same for the treatment of pain of various etiologies and other clinical indications.

BACKGROUND OF THE INVENTION

Bone pain is experienced by 75-90% of late-stage metastatic cancer patients. Metastatic cancer-induced bone pain (CIBP) is frequently reported but poorly managed. The World Health Organization implemented a three-tiered Pain-Relief-Ladder for cancer pain that recommends mild-to-strong opioids as the cancer progresses. Yet, moderate-to-severe cancer pain is not adequately managed in many patients with current analgesic therapy. Opioid therapy is associated with a host of challenging side effects contributing to their failure, while diversion of prescribed opioids have led to an addiction epidemic. Recent reports suggest that opioids may exacerbate bone loss in humans and experimental animal models, indicating that opioid therapy may be counterproductive to anti-osteolytic co-therapies and CIBP management. Furthermore, prolonged opioid therapy may increase the proliferation/migration of certain cancers.

Preclinical modeling of CIBP has revealed mechanisms driving this complex disease state and lead to the identification of potential therapeutic targets. Although the bone is innervated by both sympathetic and nociceptive nerve fibers, many human tumors of the bone lack detectable nerve fibers in the tumor itself and adjacent peripheral bone. Contributors to nociceptive signaling associated with CIBP include an acidic tumor environment and the secretion of growth factors, cytokines, and chemokines from the tumor and tumor-associated cells, as well as enhanced nerve sprouting in the local environment.

The bone is innervated by both sympathetic and nociceptive nerve fibers. However, many human bone tumors lack detectable nerve fibers within the tumor itself and the adjacent peripheral bone. Contributors to nociceptive signaling associated with CIBP include an acidic tumor environment and the secretion of growth factors, cytokines, and chemokines from the tumor and tumor-associated cells, as well as enhanced nerve sprouting in the local environment. Thus, there is a need to develop non-opioid analgesics for the treatment of pain including cancer-induced bone pain.

The present inventions are based on the discovery that native Ang(1-7), related derivative polypeptides, and/or non-peptide agonists that have affinity and agonistic efficacy for the Mas receptor improve a variety of biologic, physiologic, and pathological parameters. Specifically, it is shown that Mas receptor activation attenuates spatial memory and object recognition impairment caused by congestive heart failure (CHF), pain of various etiologies including cancer-induced bone pain and the neurological sequelae of traumatic brain injury (TBI).

SUMMARY OF THE INVENTION

Some aspects of the invention provide an oligopeptide that is angiotensin-(1-7), i.e., "Ang-(1-7)", derivative. Oligopeptides of the invention have a longer in vivo half-life and/or increased blood-brain barrier penetration than Ang-(1-7). In some embodiments, the oligopeptides of the invention have seven or eight amino acids.

One particular aspect of the invention provides an oligopeptide derivative of the formula: $A^1$-$A^2$-$A^3$-$A^4$-$A^5$-$A^6$-$A^7$-$A^8$ (SEQ ID NO:1), where $A^1$ is selected from the group consisting of aspartic acid, glutamic acid, alanine, and a derivative thereof; $A^2$ is selected from the group consisting of arginine, histidine, lysine, and a derivative thereof; $A^3$ is selected from the group consisting of valine, alanine, isoleucine, leucine, and a derivative thereof; $A^4$ is selected from the group consisting of tyrosine, phenylalanine, tryptophan, and a derivative thereof; $A^5$ is selected from the group consisting of isoleucine, valine, alanine, leucine, and a derivative thereof; $A^6$ is selected from the group consisting of histidine, arginine, lysine, and a derivative thereof; $A^7$ is selected from the group consisting of proline, glycine, serine, and a derivative thereof; and $A^8$ can be present or absent, wherein when $A^8$ is present, $A^8$ is selected from the group consisting of serine, threonine, hydroxyproline, and a derivative thereof, provided (i) at least one of $A^1$-$A^8$ is optionally substituted with a mono- or di-carbohydrate; or (ii) when $A^8$ is absent: (a) at least one of $A^1$-$A^7$ is substituted with a mono- or di-carbohydrate, (b) $A^7$ is terminated with an amino group, or (c) a combination thereof.

In some embodiments, carbohydrate comprises glucose, galactose, xylose, fucose, rhamnose, lactose, cellobiose, melibiose, or a combination thereof. In another embodiment, $A^8$ is serine or a derivative thereof.

Still in other embodiments, (i) $A^8$ is terminated with an amino group; or (ii) when $A^8$ is absent, $A^7$ is terminated with an amino group. Within these embodiments, in some instances (i) $A^8$ is serine that is glycosylated with glucose or lactose; or (ii) when $A^8$ is absent, $A^7$ is serine that is glycosylated with glucose or lactose. Still in other instances, when $A^8$ is absent and $A^7$ serine that is glycosylated with glucose. Within the latter instances, in some cases $A^7$ is terminated with an amino group.

Yet in other embodiments, $A^1$ is aspartic acid; $A^2$ is arginine; $A^3$ is valine; $A^4$ is tyrosine; $A^5$ is isoleucine; $A^6$ is histidine; and (i) $A^8$ is absent and $A^7$ is terminated with an amino group or $A^7$ is a glycosylated serine, or (ii) $A^8$ is serine terminated with an amino group. Within these embodiments, in some cases $A^8$ is a glycosylated serine. Still in other cases, $A^8$ is absent and $A^7$ is a glycosylated serine that is terminated with an amino group.

Another aspect of the invention provides a glycosylated Ang-(1-7) derivative having eight amino acids or less, typically seven or eight amino acids (e.g., amino acid residues). In some embodiments, the glycosylated Ang-(1-7) derivative is glycosylated with xylose, fucose, rhamnose, glucose, lactose, cellobiose, melibiose, or a combination thereof. Still in other embodiments, the carboxylic acid end of said glycosylated Ang-(1-7) derivative is substituted with an amino group.

Other aspects of the invention provide methods for treating cognitive dysfunction and/or impairment in a subject by administering a therapeutically effective amount of an oligonucleotide of the invention. In general, oligopeptides of the invention can be used to treat any clinical condition that can be treated with Ang-(1-7).

In some embodiments, the oligopeptides of the invention may be used to treat (i.e., reduce or eliminate) pain of any etiology (i.e., a painful condition). Specific pain syndromes and painful conditions amenable to treatment include, for example, cancer-induced bone pain from caused by either a primary or metastatic tumor, post-surgical pain, post herpatic neuralgia, fibromyalgia, inflammatory pain, stroke-induced pain, trauma-based neuropathic pain, multiple sclerosis-induced pain, rheumatoid arthritis, and complex regional pain syndrome (CRPS). The oligopeptides of the invention also may be used to treat pain and other symptoms and conditions associated with HIV-induced neuropathy, diabetic neuropathy, and chemotherapeutic neuropathy.

In other embodiments, the oligopeptides of the invention may be used to reduce or eliminate one or more symptoms of cognitive impairment including, for example, reduced attention, memory loss, psychomotor slowing, and diminished executive function. Specific conditions that are associated with cognitive impairment and that are amenable to treatment using the inventive oligopeptides include, for example, congestive heart failure, cardiovascular disease, hypertension, stroke, post-operative cognitive defects and/or delerium, dementia including age-related dementia, Alzheimer's disease, and traumatic brain injury including concussion and penetrating brain injury.

In some embodiments, the inventive oligopeptides are administered at a dosage of about 0.1-50 mg/kg, including for example at least about 0.25, 0.50, 0.75, 1.0, 1.5, 2.0, 2.5, 3.0, 4.0, 5.0, 10, 15, 20, 25, 30, or 40 mg/kg. The oligopeptides may be administered QD, bid, tid, qid, or more as necessary to obtain the desired clinical outcome. The oligopeptides may be administered orally or by injection (intravenous, subcutaneous, intramuscular, intraperitoneal, intracerebroventricular, or intrathecal), or by inhalation.

BRIEF DESCRIPTION OF THE DRAWINGS

FIG. 11A is a Western blot showing Mas receptor expression in dorsal root ganglia of nociceptive fibers in experimental animals.

FIG. 11B is a bar graph showing the relative expression of the Mas receptor between the ipsilateral and contralateral dorsal root ganglia in experimental animals.

FIG. 11C is a Western blot showing Mas receptor expression in femoral exudate of experimental animals.

FIG. 11D is a bar graph showing the relative expression of the Mas receptor between the ipsilateral and contralateral femoral exudate in experimental animals.

FIG. 13A is a series of radiographs taken from experimental animals.

FIG. 13B is a graph quantifying bone lesion scoring in experimental animals.

FIG. 13C is a bar graph showing the amount of carboxy-terminal collagen crosslinks as a measure of bone integrity in experimental animals.

DETAILED DESCRIPTION OF THE INVENTION

Definitions

Figure 1:
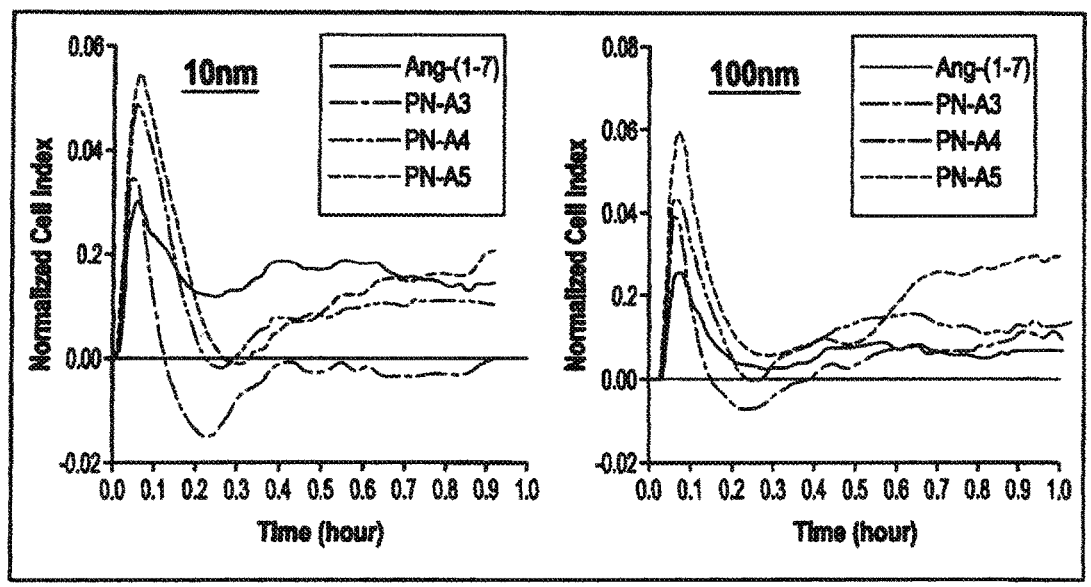
FIG. 1 is a graph showing some of the oligopeptides of the invention and native Ang-(1-7) to activate human umbilical vascular endothelial cells (HUVEC) in culture.

The term "native" refers to any sequence of L amino acids used as a starting sequence or a reference for the preparation of partial or complete retro, inverso or retro-inverso analogues. Thus, the term "native Ang-(1-7)" refers to an oligopeptide having the same amino acid sequence as that of endogenous Ang-(1-7). It should be appreciated that the use of the term "native" does NOT imply naturally occurring, although it can include naturally occurring Ang-(1-7). The term "native" merely refers to having the same amino acid sequence as that of Ang-(1-7) without any modification of the amino acid residues. Accordingly, the term "native Ang-(1-7)" includes both synthetic Ang-(1-7) and naturally occurring Ang-(1-7) as long as the amino acid residues are the same and are not modified.

The term "Ang-(1-7) derivative" refers to oligopeptide in which one or more amino acid residue is either modified or different than the amino acid residue of the corresponding native Ang-(1-7). The term "Ang-(1-7) derivative" also includes oligopeptide of eight amino acid residues as discussed in more detail below.

The term "retro modified" refers to a peptide which is made up of L-amino acids in which the amino acid residues are assembled in opposite direction to the native peptide with respect the which it is retro modified. The term "inverso modified" refers to a peptide which is made up of D-amino acids in which the amino acid residues are assembled in the same direction as the native peptide with respect to which it is inverso modified. The term "retro-inverso modified" refers to a peptide which is made up of D-amino acids in which the amino acid residues are assembled in the opposite direction to the native peptide with respect to which it is retro-inverso modified. Thus, native Ang-(1-7) (L-amino acids, N→C direction) is: Asp-Arg-Val-Tyr-Ile-His-Pro, i.e., DRVYIHP (SEQ ID NO:2). Retro-inverso Ang-(1-7) (D-amino acids, C→N direction) is: DRVYIHP (SEQ ID NO:3). Retro Ang-(1-7) (L-amino acids, C→N direction) is: DRVYIHP (SEQ ID NO:4). And inverso Ang-(1-7) (D-amino acids, N→C direction) is: DRVYIHP (SEQ ID NO:5). The use of D-amino acids in the context of inverso modified and retro-inverso modified Ang-(1-7) derivatives is not intended to be limiting on the use of D-amino amino acids in the oligopeptides. As discussed in more detail below, fewer than all of the amino acids in an Ang-(1-7) derivative may be D-amino acids.

The term "carbohydrate" refers to pentose and hexose of empirical formula $(CH_2O)_n$, where n is 5 for pentose and 6 for hexose. A carbohydrate can be monosaccharide, disaccharide, oligosaccharide (e.g., 3-20, typically 3-10, and often 3-5 monomeric saccharides are linked together), or polysaccharide (e.g., greater than 20 monomeric saccharide units). More often, the term carbohydrate refers to mono-saccharide and/or disaccharide. However, it should be appreciated that the scope of the invention is not limited to mono- or di-saccharides. Often the terms "carbohydrate" and "saccharide" are used interchangeably herein.

The term "oligopeptide" as used throughout the specification and claims is to be understood to include amino acid chain of any length, but typically amino acid chain of about fifteen or less, often ten or less, still more often eight or less, and most often seven or eight.

It should be appreciated that one or more of the amino acids of Ang-(1-7) can be replaced with an "equivalent amino acid", for example, L (leucine) can be replaced with isoleucine or other hydrophobic side-chain amino acid such as alanine, valine, methionine, etc., and amino acids with polar uncharged side chain can be replaced with other polar uncharged side chain amino acids. While Ang-(1-7) comprises 7 amino acids, in some embodiments the oligopeptide of the invention has eight or less amino acids.

The term "derivative" refers to any chemical modification of the amino acid, such as alkylation (e.g., methylation or ethylation) of the amino group or the functional group on the side chain, removal of the side-chain functional group, addition of a functional group (e.g., hydroxyl group on proline), attachment of mono- or di-carbohydrate (e.g., via glycosylation) etc. Exemplary glycosylated derivatives include hydroxyl group on serine that is glycosylated with glucose, galactose, ribose, arabinose, xylose, lyxose, allose, altrose, mannose, gulose, iodose, talose, fucose, rhamnose, etc. as well as disaccharides and amino sugars such as galactosamine, glucosamine, sialic acid, N-acetyl glucosamine, etc. Amino acid derivatives also include modified or unmodified D-amino acids.

The term "combinations thereof," which reference to any modifications (e.g, carbohydrate modifications) of Ang-(1-7) derivatives refers to oligopeptides in which two, three, four, five, six, seven, or eight of the individual amino acids are modified by the attachment of a carbohydrate. For Ang-(1-7) derivatives having a plurality of carbohydrate modifications, the modifying carbohydrates may be the same on every modified amino acid, or the several modified amino acids may comprise a mixture of different carbohydrates.

"A therapeutically effective amount" means the amount of a compound that, when administered to a mammal, at an appropriate interval and for a sufficient duration for treating a disease, is sufficient to effect such treatment for the disease. The "therapeutically effective amount" will vary depending on the compound, the disease and its severity, physiological factors unique to the individual including, but not limited to the age, weight, and body mass index, the unitary dosage, cumulative dosage, frequency, duration, and route of administration selected.

As used herein, the term "treating", "contacting" or "reacting" when referring to chemical synthesis means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "treating" and "treatment" refer to effecting an improvement of any symptom or physiological, cognitive, or biochemical indicium of the condition or disease being treated. For example, treatment of a cognitive dysfunction and/or impairment may refer to: (1) preventing cognitive dysfunction and/or impairment from occurring, i.e., causing the clinical symptoms of cognitive dysfunction and/or impairment not to develop in a subject that may be or predisposed to developing cognitive dysfunction and/or impairment but does not yet experience or display symptoms of cognitive dysfunction and/or impairment; (2) inhibiting cognitive dysfunction and/or impairment, i.e., arresting or reducing the development of cognitive dysfunction and/or impairment or its clinical symptoms; or (3) relieving cognitive dysfunction and/or impairment, i.e., causing regression of cognitive dysfunction and/or impairment or its clinical symptoms.

The terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "subject" or "patient" refers to any organism to which a composition of this invention may be administered, e.g., for experimental, diagnostic, and/or therapeutic purposes. Typical subjects include animals (e.g., mammals such as mice, rats, rabbits, dogs, cats, non-human primates, and humans).

Unless defined otherwise, all technical and scientific terms used herein have the meaning commonly understood by a person skilled in the art to which this invention belongs.

Oligopeptides of the Invention:

The renin-angiotensin system (RAS), well known for roles in blood pressure regulation and fluid homeostasis, was recently implicated in metastatic bone disease including inflammation, angiogenesis, tumor cell proliferation, and migration. Angiotensin II (Ang II) is the major end product of the RAS through cleavage by Angiotensin Converting Enzyme (ACE). This nonapeptide binds to and activates two G-protein coupled receptors (GPCRs): angiotensin II receptor type 1 (AT1) and type 2 (AT2). Physiological effects such as vasoconstriction, inflammation, fibrosis, cellular growth/migration, and fluid retention are reported for AT1 and AT2. Ang II is cleaved by ACE2 to yield Angiotensin-(1-7) (Ang-(1-7)), a biologically active heptapeptide. In contrast to Ang II, Ang-(1-7) binds to the GPCR, Mas receptor (MasR; Kd=0.83 nM) with 60-100 fold greater selectivity over the AT1 and AT2 receptors. Activation of the MasR elicits effects opposite to those of the Ang II/AT1/AT2 axis including having anti-inflammatory and antidepressant activities.

Some aspects of the invention provide oligopeptides that are derivatives of Ang-(1-7). As discussed above, the term "derivative" of Ang-(1-7) refers to an oligopeptide whose amino acid sequence of any one or more of Ang-(1-7) is modified (e.g., via methylation, presence of a functional group, such as hydroxy group on proline), attached to a carbohydrate, is replaced with corresponding D-amino acid or an "equivalent amino acid" as defined above, and/or the terminal amino group end or the carboxyl end of Ang-(1-7) is modified, for example, the carboxylic acid end can be modified to be an amide, an amine, a thiol, or an alcohol functional group, or one in which an additional amino acid residue is present compared to native Ang-(1-7). It should be appreciated that the term "Ang-(1-7) derivative" excludes the native Ang-(1-7), i.e., amino acid sequences of endogenous Ang-(1-7) without any modification.

In some embodiments, oligopeptides of the invention have the amino group on the carboxylic acid terminal end (i.e., the —OH group of the carboxylic acid is replaced with —NR$^a$R$^b$, where each of R$^a$ and R$^b$ is independently hydrogen or $C_1$-$C_6$ alkyl) and/or have one or more amino acid residues that are (i) replaced with a corresponding D-amino acid, (ii) glycosylated, (iii) replaced with another amino acid, (iv) or a combination thereof.

Still in other embodiments, the oligopeptide of the invention is retro-inverso Ang-(1-7). Yet in other embodiments, the oligopeptide of the invention is retro Ang-(1-7). In other embodiments, the oligopeptide of the invention is inverso Ang-(1-7).

Other embodiments of the invention include Ang-(1-7) derivatives in which at least one or more, typically one or two, and often only one amino acid is attached to a carbohydrate. Generally, the carbohydrate is attached to the amino acid via glycosylation. Typically, the carbohydrate is a mono- or di-carbohydrate. Exemplary mono- and di-carbohydrates that can be used in the invention include, but are not limited to, xylose, fucose, rhamnose, glucose, lactose, cellobiose, melibiose, and a combination thereof.

In one particular embodiment, the oligopeptide of the invention is Ang-(1-7) derivative of the formula: $A^1$-$A^2$-$A^3$-$A^4$-$A^5$-$A^6$-$A^7$-$A^8$ (SEQ ID NO:1), where $A^1$ is selected from the group consisting of aspartic acid, glutamic acid, alanine, and a derivative thereof; $A^2$ is selected from the group consisting of arginine, histidine, lysine, and a derivative thereof; $A^3$ is selected from the group consisting of valine, alanine, isoleucine, leucine, and a derivative thereof; $A^4$ is selected from the group consisting of tyrosine, phenylalanine, tryptophan, and a derivative thereof; $A^5$ is selected from the group consisting of isoleucine, valine, alanine, leucine, and a derivative thereof; $A^6$ is selected from the group consisting of histidine, arginine, lysine, and a derivative thereof; $A^7$ is selected from the group consisting of proline, glycine, serine, and a derivative thereof; and $A^8$ can be present or absent, wherein when $A^8$ is present, $A^8$ is selected from the group consisting of serine, threonine, hydroxyproline, and a derivative thereof, provided (i) at least one of $A^1$-$A^8$ is optionally substituted with a mono- or di-carbohydrate; or (ii) when $A^8$ is absent: (a) at least one of $A^1$-$A^7$ is substituted with a mono- or di-carbohydrate, (b) $A^7$ is terminated with an amino group, or (c) a combination thereof.

In some embodiments, $A^1$ is the amino terminal end of the oligopeptide and $A^8$ (or $A^7$ when $A^8$ is absent) is the carboxyl terminal end. Still in other embodiments, $A^1$ is the carboxyl terminal end and $A^8$ (or $A^7$ when $A^8$ is absent) is the amino terminal end. Yet in other embodiments, the carboxylic acid functional group of the carboxyl terminal end is modified as an amide functional group, an amine functional group, a hydroxyl functional group, or a thiol functional group. The amide and the amine functional groups can be non-alkylate, mono-alkylated or di-alkylated.

Yet in other embodiments, the carbohydrate comprises glucose, galactose, xylose, fucose, rhamnose, or a combination thereof. In some instances, the carbohydrate is a mono-carbohydrate, whereas in other instances, the carbohydrate is a di-carbohydrate.

In other embodiments, at least one of $A^1$-$A^8$ is substituted with a mono-carbohydrate. Still in other embodiments, at least one of $A^1$-$A^8$ is substituted with a di-carbohydrate. It should be appreciated that the scope of the invention also includes those oligopeptides having both mono- and di-carbohydrates.

Exemplary di-carbohydrates that can be used in oligopeptides of the invention include, but are not limited to, lactose, cellobiose, melibiose, and a combination thereof. However, it should be appreciated that the scope of the invention includes oligopeptides that are substituted with any dicarbohydrates known to one skilled in the art.

In one particular embodiment, $A^8$ is serine or a derivative thereof. In some instances, the carboxylic acid moiety of the serine is modified as an amide or an amine. In one case, serine is terminated as an amino group. Still in other embodiments, the serine residue of $A^8$ is glycosylated with glucose or lactose.

Yet in other embodiments, at least one, typically at least two, generally at least three, often at least four, still more often at least five, yet still more often at least six, and most often all of $A^1$-$A^8$ is D-amino acid.

In particular, in some specific embodiments, said oligopeptide is retro modified, inverso modified, or retro-inverso modified.

Another aspect of the invention provides oligopeptides, such as Ang-(1-7) derivatives, having eight amino acids or less, typically seven or eight amino acid residues. In some embodiments, one or more amino acids have attached thereto a carbohydrate group. Often the carbohydrate group is attached to the oligopeptide via glycosylation. The carbohydrate can be attached to the oligopeptide via any of the side chain functional group of the amino acid or the amide group. Accordingly, the scope of the invention includes, but is not limited to, O-glycosylate, N-glycosylate, S-glycosylated oligopeptides. The term "X-glycosylated" refers to having a carbohydrate attached to the oligopeptide via the heteroatom "X" of the amino acid. For example, for serine whose side-chain functional group is hydroxyl, "O-glycosylated" means the carbohydrate is attached to the serine's side-chain functional group, i.e., the hydroxyl group. Similarly, "N-glycosylation" of leucine refers to having the carbohydrate attached to the amino side-chain functional group of leucine. Typically, the glycosylation is on the side-chain functional group of the amino acid.

In some embodiments, the Ang-(1-7) derivative is glycosylated with xylose, fucose, rhamnose, glucose, lactose, cellobiose, melibiose, or a combination thereof.

Yet in other embodiments, the carboxylic acid terminal end of said glycosylated Ang-(1-7) derivative is substituted with an amino group. When referring to the carboxyl acid terminal end being substituted with an amino group, it means —OH group of the carboxylic acid is replaced with —$NH_2$ group. Thus, the actual terminal end functional group is an amide, i.e., rather than having the oligopeptide being terminated at the carboxylic acid terminal end with a functional group —$CO_2H$, the carboxylic acid terminal end is terminated with an amide group (i.e., —$CO_2NR'_2$, where each R' is independently hydrogen or $C_1$-$C_{12}$ alkyl). Still in other embodiments, the carboxylic acid terminal group is terminated with a hydroxyl or a thiol group. In some embodiments, the modified carboxylic acid terminal group is used to attach the carbohydrate, e.g., via glycosylation.

One of the purposes of the invention was to produce Ang-(1-7) derivatives to enhance efficacy of action, in vivo stabilization, and/or penetration of the blood-brain barrier. Improved penetration of the blood-brain barrier facilitates cerebral entry of the Ang-(1-7) derivative of the invention, and, consequently, Mas activation, or intrinsic-efficacy. To improve (i.e., increase) penetration of the blood-brain barrier, in some embodiments the Ang-(1-7) derivative is attached to at least one mono- or di-carbohydrates.

Without being bound by any theory, it is believed that the oligopeptide of the invention that are glycosylated exploits the inherent amphipathicity of the folded Ang-(1-7) glycopeptides (i.e., glycosylated oligopeptides of the invention) and the "biousian approach" to deliver the glycosylated oligopeptides of the invention across the blood-brain barrier. In some instances, the amount of increase in crossing the blood-brain barrier by oligopeptides of the invention is at least 6%, typically at least 10%, and often at least 15% compared to native Ang-(1-7). In some instances, the amount of increase in the Cmax for oligopeptides of the invention in cerebral-spinal fluid is 2-10 fold, 3-8 fold, or 5-8 fold compared to native Ang-(1-7). In some instances, the amount of increase in the Cmax for oligopeptides of the invention in cerebral-spinal fluid is 2, 3, 4, 5, 6, 7, 8, 9 or 10 fold compared to native Ang-(1-7). In other instances, oligopeptides of the invention have in vivo half-life of at least 20 min, at least 30 min, at least 40 min, at least 50 min, at least 60 min, or at least 2, hours, at least 3 hours, at least 4 hours, at least 5 hours or at least 6 hours. In some instances, the amount of increase in the in vivo half-life for oligopeptides of the invention is 2-30 fold, 3-25 fold, 4-20 fold, 4-10 fold, 10-25 fold, 15-25 fold, or 20-25 fold compared to native Ang-(1-7). Alternatively, compared to native Ang-(1-7), oligopeptides of the invention exhibit at least 50 fold, typically at least 75 fold, and often at least 100 fold increase in in vivo half-life.

In other embodiments, oligopeptides of the invention exhibit enhanced vascular efficacy. Without being bound by any theory, it is generally recognized that blood-brain barrier transport occurs via an absorptive endocytosis process on the blood side of the endothelium of the brain capillaries followed by exocytosis on the brain side, leading to overall transcytosis. It is also believed that for this process to be efficient, the oligopeptide must bind to the membrane for some period of time, and must also be able to exist in the aqueous state for some period of time (biousian nature). Based on previous work from one of the present inventors, it is believed that effective drug delivery and blood-brain barrier transport requires a biousian glycopeptide that has at least two states: (1) a state defined by one or more membrane-bound conformations that permit or promote endocytosis; and (2) a state defined by a water-soluble, or random coil state that permits "membrane hopping" and, presumably, vascular efficacy.

In general, the degree of glycosylation does not have a large effect on the structure of the individual microstates. Thus, altering the degree of glycosylation allows for the modulation of aqueous vs. membrane-bound state population densities without significantly affecting the overall structure of the oligopeptide. Moreover, it is believed that glycosylation also promotes stability to peptidases, thereby increasing the half-life of the Ang-(1-7) derivatives in vivo.

TABLE 1

Some of the representative oligopeptides of the invention.

|  | 1 | 2 | 3 | 4 | 5 | 6 | 7 | 8 | carboxyl terminal end functional group |
|---|---|---|---|---|---|---|---|---|---|
| Native $AT_{1-7}$ | Asp | Arg | Val | Tyr | Ile | His | Pro | — | OH (SEQ ID NO: 2) |
| PN-A1 | Asp | Arg | Val | Tyr | Ile | His | Pro | — | $NH_2$ (SEQ ID NO: 6) |
| PN-A2 | Asp | Arg | Val | Tyr | Ile | His | Pro | Ser° | $NH_2$ (SEQ ID NO: 7) |
| PN-A3 | Asp | Arg | Val | Tyr | Ile | His | Pro | Ser* | $NH_2$ (SEQ ID NO: 8) |
| PN-A4 | Asp | Arg | Val | Tyr | Ile | His | Pro | Ser** | $NH_2$ (SEQ ID NO: 9) |
| PN-A5 | Asp | Arg | Val | Tyr | Ile | His | Ser* | — | $NH_2$ (SEQ ID NO: 10) |
| PN-A6-PN-A11 | Ala | → | scan | Tyr | Ile | etc. | Pro | Ser°\*/** | $NH_2$ (SEQ ID NO: 11) |
| PN-A12 | Asp | Arg | Xxx | Tyr | Yyy | His | Pro | Ser°\*/** | $NH_2$ (SEQ ID NO: 12) |
| PN-AXX | Asp | Arg | Xxx | Zzz | Yyy | His | Pro | Ser°\*/** | $NH_2$ (SEQ ID NO: 13) |

Table 1 above shows some of the representative oligopeptides of the invention. In particular, these oligopeptides can be considered Ang-(1-7) derivatives. In Table 1, the "n-x", where x is an integer, represents the oligonucleotide identifier. For example, PN-A1 means oligopeptide number 1, PN-A2 means oligopeptide number 2, PN-A6-PN-A11 means oligopeptide numbers 6 through 11, and so forth.

Thus, the term "A-x" is used for identification purposes only. As shown in Table 1, some of the oligopeptides have carbohydrate attached to the native Ang-(1-7) peptide. These peptides are sometimes referred to as glycopeptides.

Studies have shown that inherent binding of the glycopeptide to the native receptor is minimally affected. Therefore, the glycosylated Ang-(1-7) derivatives, at a minimum, maintain Mas binding similar to that of the native Ang-(1-7) peptide. In addition, promoting the aqueous nature of the glycopeptide can further enhance vascular efficacy of Ang-(1-7) derivatives. The degree of glycosylation (e.g., Table 1: unglycosylated Ser°, glycosylated Ser* or lactosylated Ser**) for optimal blood-brain barrier transport is determined using the best binding compounds from these using the in vivo mouse model. Besides the disaccharide β-lactose, the more robust disaccharide β-cellobiose is examined using these first few structures. Based on the amino acid sequence of Ang-(1-7) and the potential modification strategies, there are at least about 200 possible derivatives of Ang-(1-7) that are rapidly generated using the well known oligopeptide synthesis, including automated peptide synthesis as well as combinatorial synthesis.

Cognitive Dysfunction

Cognitive dysfunction or impairment is a common neurological complication of congestive heart failure ("CHF") and post cardiac surgery affecting approximately 50-70% of patients at hospital discharge and 20-40% of patients six months after surgery. The occurrence of CHF and postoperative cognitive dysfunction is associated with increased duration of hospitalization and impaired long-term quality of life. Without being bound by any theory, it is believed that in general any clinical condition associated with an increase in inflammatory cytokines and/or increase in reactive oxygen species in central nervous system, in particular in the brain, can lead to cognitive dysfunction.

Other aspects of the invention provide methods for treating cognitive dysfunction and/or impairment in a patient using an oligopeptide of the invention. Typically, methods of the invention include administering to a patient in need of such a treatment a therapeutically effective amount of an oligopeptide of the invention. It should be appreciated that the oligopeptides of the invention can be used to treat any clinical conditions that are known to be treatable or appears to be treatable using Ang-(1-7). However, for the sake or clarity and brevity, the invention will now be described in reference to treating cognitive dysfunction and/or impairment in a patient.

The cognitive dysfunction that occurs in congestive heart failure (CHF) patients includes decreased attention, memory loss, psychomotor slowing, and diminished executive function, all of which compromises patients' ability to comply with complex medical regimens, adhere to dietary restrictions and make self-care decisions. Mechanisms thought to contribute to cognitive impairment in patients with CHF include changes in cerebral blood flow, altered cerebrovascular autoregulation and microembolisms. In one study, cerebral blood flow was measured with single-photon emission computed tomography (SPECT) and found to be reduced by 30% in patients with severe heart failure. The causes for decreased cerebral perfusion in CHF have been attributed to low cardiac output, low blood pressure and altered cerebrovascular reactivity. In some cases, the cognitive impairment seen in CHF is improved following either heart transplant or improvement in cerebral blood flow via optimal management of CHF. However, for many patients with CHF, management is rarely optimal and the cognitive impairment persists. Interestingly, long-term follow up studies have revealed that cognitively normal CHF patients have a significantly higher risk of dementia or Alzheimer's disease compared to age-matched non-CHF controls, suggesting that CHF and cardiovascular disease predispose patients to further cognitive impairment and dementia.

During CHF, the well characterized changes in the circulating neurochemical milieu and increases in inflammatory factors are also seen in the brain. Most of the studies on CHF-induced changes in inflammatory cytokines and ROS have focused on brain regions involved in sympathetic outflow regulation and not on cognition. CHF elevates sympathetic tone and causes abnormal cardiac and sympathetic reflex function. In the rat, ischemia-induced CHF significantly increases pro-inflammatory cytokines and Angiotensin II type 1 receptors (AT1) in the paraventricular nucleus (PVN) of the hypothalamus. Further, in CHF rabbits, the increase in sympathetic outflow is blocked by ICV injection of the super oxide dimustase (SOD) mimetic tempol, presumably by inhibition of ROS. CHF in this model is associated with increased expression of NADPH oxidase subunits and ROS production in the rostral ventral lateral medulla (RVLM) and increases in NO.

The role of ROS in learning and memory has been extensively studied. All of the NAD(P)H oxidase subunits, including NOX2 and NOX4, have been localized within the cell bodies and dendrites of neurons of the mouse hippocampus and perirhinal cortex and are co-localized at synaptic sites. These are key regions of the brain in learning and memory. In the brain, superoxide production via actions of NAD(P)H oxidase are known to be involved in neurotoxicity, age related dementia, stroke and neurodegenerative diseases and have been identified throughout the brain including the hippocampus, thalamus, cerebellum and amygdala. In younger, healthy animals ROS and NAD(P)H oxidase is shown to be required for normal learning and hippocampal long-term potentiation (LTP). Recent studies in mice lacking Mas have shown that Ang-(1-7) and Mas are essential for normal object recognition processing and blockade of Mas in the hippocampus impairs object recognition. In addition, Ang-(1-7) facilitates LTP in CA1 cells and this effect is blocked by antagonism of Mas. In older animals or in CHF animals, an increase in ROS is linked to LTP and memory impairments.

Over the last decade, it has become recognized that renin angiotensin system (RAS) involves two separate enzymatic pathways providing a physiological counterbalance of two related peptides acting at distinct receptors. The well described ACE-AngII-AT1 receptor system is thought to be physiologically opposed and balanced by the ACE2-Ang-(1-7)-Mas system. Functionally, these two separate enzymatic pathways of RAS are thought to be involved in balancing ROS production and nitric oxide (NO) in the brain, microvasculature and peripheral tissues. Increases in AT1 receptor activation are known to increase NAD(P)H oxidase and ROS generation which are both known to contribute to abnormal increases of sympathetic nerve activity observed in CHF and hypertension. This increase in AT1 receptor-induced ROS formation is thought to be opposed by ACE2-Ang-(1-7)-Mas inhibition of ROS formation. Ang-(1-7), the majority of which is produced from ACE2 cleavage of Ang II, decreases ROS production and increases NOS in the brain via activation Mas and, possibly through AT2 receptor.

Within the brain, the Mas receptor is known to be expressed on neurons, microglia and vascular endothelial cells. Further, all three of these key components that make up the "neurovascular unit" (neurons, microglia and endothelial cells) are central players in neurogenic hypertension and CHF-induced increases in brain inflammation and ROS production. Both CHF and hypertension increase circulating cytokines promoting ROS production within the "neurovascular unit". The end-result of this feed-forward cascade is neuronal dysfunction and cognitive impairment. The ideal therapeutic candidate to treat cognitive impairment would be designed to interrupt this cascade by working at both sides of the blood-brain barrier, the brain vascular endothelium and neuronal cells. Ang-(1-7), acting at the Mas receptor, is known to have effects at both endothelial cells and neurons. However, using a native Ang-(1-7) for treating cognitive dysfunction and/or impairment is not suitable because native Ang-(1-7) is susceptible to enzymatic degradation. Moreover, native Ang-(1-7) does not readily cross the blood-brain barrier to be suitable as a therapeutic agent.

Without being bound by any theory, it is believed that one of the advantages of using oligopeptides of the invention in treating cognitive dysfunction and/or impairment is that oligopeptides of the invention have enhanced endothelial "interaction" and brain penetration. It is believed that oligopeptides of the invention act at both endothelial cells and neurons thus inhibiting inter alia neurovascular ROS production and mitigating the brain inflammatory cascade.

Accordingly, oligopeptides the invention can be used to treat cognitive impairment and/or dysfunction (1) associated with pre- and/or post-surgery dementia, or (2) observed in patients with congestive heart failure, cardiovascular disease, or hypertension. More generally, oligopeptides of the invention are useful in treating cognitive dysfunction and/or impairment in a subject whose cognitive dysfunction and/or impairment is clinically associated with an increase in inflammatory cytokines and/or increase in reactive oxygen species ("ROS") in the central nervous system, in particular the brain. As used herein, the term "clinically associated" refers to the root cause or underlying cause of cognitive dysfunction and/or impairment (such as, but not limited to, memory loss) that when ameliorated results in reduction, prevention, treatment or reversal of cognitive dysfunction and/or impairment. Exemplary clinical conditions associated with an increase in inflammatory cytokines and/or increase in reactive oxygen species that can cause cognitive dysfunction and/or impairment include, but are not limited to, circulatory compromise, cardiovascular disease, hypertension, hypotension, congestive heart failure, stroke, embolism, surgery (e.g., postoperative recovery condition), dementia, Alzheimer's disease, disease related cognitive impairment, trauma related cognitive impairment, age-related dementia, postoperative related delirium and/or increase in inflammatory cytokine and/or increase in reactive oxygen species within the central nervous system of said subject or a combination thereof.

Anti-Nociception and Analgesia

The inventions described herein are based, in part, on the discovery that Mas receptor agonists, including the prototypical native Ang(1-7) polypeptide, induce analgesia. As described herein, the analgesic properties of Ang-(1-7) was evaluated in a CIBP as a representative model of nociceptive conditions. It is demonstrated that acute and chronic systemic administration of Ang-(1-7) significantly reduced the spontaneous pain behaviors associated with CIBP. Importantly, repeated administration attenuated CIBP without loss of efficacy after 7 days. However, no significant change in nesting behaviors with or without treatments was observed, suggesting that the nesting is not representative of possible anxiety or depression in mice with CIBP.

To confirm that the effects of Ang(1-7) are mediated by the Mas receptor, control experiments using the Mas receptor antagonist, A-779, were performed. The inhibition of guarding and flinching by Ang(1-7) were significantly prevented by administration of A-779.

Repeated Ang-(1-7) administration did not significantly alter the expression of MasR in the DRGs or femur extrudate demonstrating that repeated Ang-(1-7) dosing does not significantly alter MasR expression in the DRGs containing soma of fibers innervating the bone-tumor microenvironment. Consistent with these findings, analgesic tolerance was not observed over the treatment paradigm.

It also was discovered that pre-administration of an AT1 receptor antagonist, Losartan potassium, further alleviates cancer-induced bone pain, yet by itself had no significant effect. It is hypothesized that Losartan augments the effect to Ang-(1-7) in CIBP because AT1 antagonism inhibits Ang-(1-7) from acting similarly to Ang II at AT1, thereby allowing Ang-(1-7) to bind primarily to MasR to induce analgesia. The AT2 antagonist, PD 123319, did not attenuate the effects of Ang-(1-7) nor result in enhanced pain relief, indicating that the AT2 receptor does not play a role in CIBP. In addition, the Ang-(1-7) did not demonstrate any changes in motor activity by measuring the amount of time animals that received Ang-(1-7) remained walking on a slow rotating rod.

In sum, these data demonstrate that Ang-(1-7) at the Mas receptor is for inhibiting pain in the tumor-nociceptor microenvironment. Ang-(1-7) did not significantly change the tumor-induced degradation of the bone nor did it significantly alter tumor proliferation, further suggesting the analgesic effect is directly towards inhibiting nociceptive activation and not due to changes in tumor burden. Mas receptor agonists such as Ang(1-7) therefore induce primary analgesia through pharmacologic mechanisms rather than secondarily through effects on the bone tissue or anti-neoplastic activity. Thus, Mas receptor agonists may attenuate pain and the behavioral signs of pain in conditions other than CIBP.

Methods of Administration

Oligopeptides of the present invention can be administered to a patient to achieve a desired physiological effect. Preferably the patient is an animal, more preferably a mammal, and most preferably a human. The oligopeptide can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active oligopeptide can be orally administered, for example, with an inert diluent or with an assimilable edible carrier, or it can be enclosed in hard or soft shell gelatin capsules, or it can be compressed into tablets. For oral therapeutic administration, the active oligopeptide may be incorporated with excipient and used in the form of ingestible tablets, buccal tablets, troches, capsules, elixirs, suspensions, syrups, wafers, and the like. Such compositions and preparation can contain at least 0.1% of active oligopeptide. The percentage of the compositions and preparation can, of course, be varied and can conveniently be between about 1 to about 10% of the weight of the unit. The amount of active oligopeptide in such therapeutically useful compositions is such that a suitable dosage will be obtained.

Preferred compositions or preparations according to the present invention are prepared such that an oral dosage unit form contains from about 1 to about 1000 mg of active oligopeptide.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active oligopeptide, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active oligopeptide can be incorporated into sustained-release preparations and formulation.

The active oligopeptide can also be administered parenterally. Solutions of the active oligopeptide can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active oligopeptide in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic oligopeptides of the present invention can be administered to a mammal alone or in combination with pharmaceutically acceptable carriers, as noted above, the proportion of which is determined by the solubility and chemical nature of the oligopeptide, chosen route of administration and standard pharmaceutical practice.

The physician will determine the dosage of the present therapeutic agents which will be most suitable for prophylaxis or treatment and it will vary with the form of administration and the particular oligopeptide chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Ang-(1-7) Derivative High-Throughput Screening (HTS)

For HTS, a sensitive and direct measure of nitric oxide (NO) production in 2 separate cell lines is utilized, primary CA1 hippocampal neurons and human umbilical vein endothelial cells (HUVEC). The use of primary CA1 cells is self-evident for the study of central effects. In addition, the contribution of endothelial dysfunction to the progression of CHF and to the induction of cognitive impairment is clinically appreciated. The emerging picture that the Ang-(1-7) singling axis holds promise as a therapeutic target for endothelial dysfunction strongly indicates that reversal of CHF-induced endothelial dysfunction as mechanism cannot be ruled out. HUVEC are isolated from the human umbilical vein and cryo-preserved after primary culture. HUVEC is included as a second line for the primary screen because these cells are the model in vitro system for the study of endothelial cell function and can be used to directly measure Mas-dependent NO production.

Cell culture. To isolate primary hippocampal CA1 neuronal cells, whole brain was removed from neonatal rat pups (1-2 day old) and the cortices dissected away. The hippocampus was isolated and the CA1 field was excised and placed in buffer. After gentle disruption in digestion buffer, the cells were counted, placed in culture media, and plated in a 96-well format coated with poly-d-lysine. At the time of plating, cells were approximately at 50% density and were allowed to culture to 70-80% density before starting the assay. Commercially available HUVEC (Life Technologies/Thermo Fisher) was thawed and plated (5000-10,000 cells/ well) in a 96-well format coated with gelatin. HUVEC cells were allowed to culture overnight before starting the assay.

Cell Activation: The xCELLigence system Real-Time Cell Analyzer (RTCA), developed by Roche Applied Science, uses microelectronic biosensor technology to do dynamic, real-time, label-free, and non-invasive analysis of cellular events including G-protein receptor activation of cells. The RTCA analysis was utilized to measure the potency and relative ability of oligopeptides of the invention and native Ang-(1-7) to activate human umbilical vascular endothelial cells (HUVEC) in culture. Following uniform cellular adherence based on a linear increase in cell impedance (CI), HUVECs were treated with Ang-(1-7) and oligopeptides of the invention. Each trace of the CI over time in FIG. 1 represents the average of 4 wells normalized to CI at the time of compound addition. FIG. 1 shows the results from data acquired using the xCELLigence RTCA to measure the relative potency of PN-A3, PN-A4, PN-A5 and native Ang-(1-7). A 100 nM administration of PN-A3, PN-A4 and PN-A5 and 10 nM of PN-A3 and PN-A5 resulted in a significant (~2-fold) increase in CI over the native Ang-(1-7) demonstrating that the oligopeptides of the invention have greater potency for cell activation than native Ang-(1-7).

NO production assay. As a screen for mechanisms of action of oligopeptides of the invention, the ability to increase NO production of three oligopeptides of the invention (PN-A3, PN-A4 and PN-A5) were characterized and compared to native Ang-(1-7). Human umbilical vascular endothelial cells (HUVEC) culture plates received fluorescence reaction buffer (0.2 M phosphate buffer, pH 7, 1 mM EDTA, 0.1% glucose) containing diaminofluorescein-FM diacetate (DAF-FM, 1 µM) to measure real-time NO production. Time-resolved (10 minutes) fluorescent intensity was detected using a BioTek Synergy 2 microplate reader with excitation at 485 nm and emission at 535 nm. DAF-FM is a sensitive flourometric derivative for the selective detection of NO in live cells.

Figure 2:
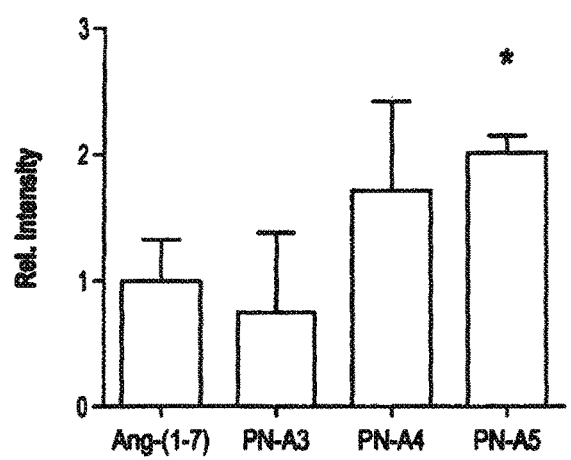
FIG. 2 is a graph showing NO production assay results for native Ang-(1-7) and oligopeptides PN-A3, PN-A4 and PN-A5 of the invention.

FIG. 2 shows relative peak fluorescence intensity following 5 minutes exposure to native Ang-(1-7) and three oligopeptides of the invention. Values were normalized to control fluorescence. As expected, native Ang-(1-7) induced a significant elevation of NO over control levels. More importantly, as shown in FIG. 2, oligopeptides of the invention (namely PN-A3, PN-A4 and PN-A5) also elicited a significant elevation of NO over control levels, with PN-A5 significantly enhancing NO production over that seen with native Ang-(1-7), *=p<0.05. These results demonstrate that oligopeptides of the invention increase NO production similar to or greater than that of native Ang-(1-7).

Figure 3A:
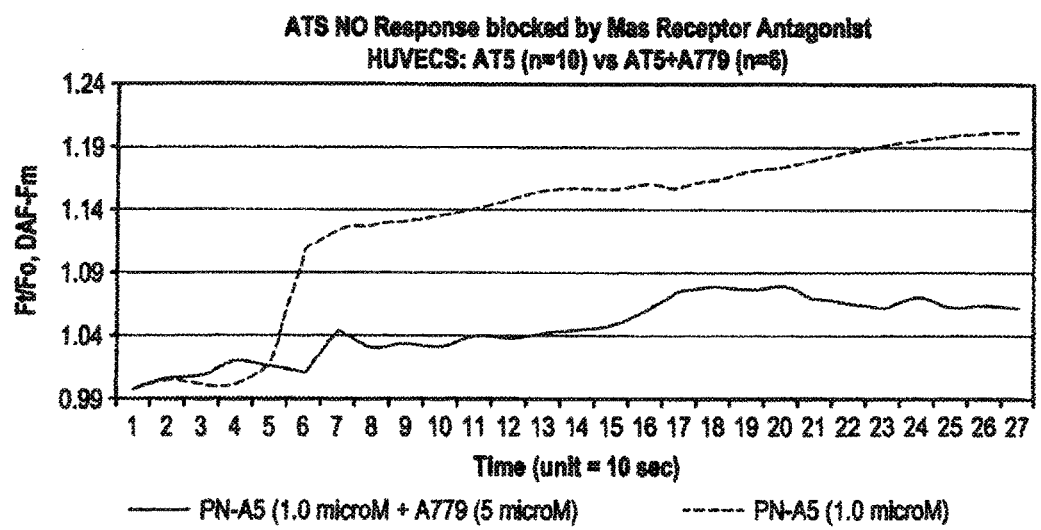
FIG. 3A is a graph showing the select Mas receptor antagonists A779 blocks NO production induced by oligopeptide PN-A5 of the invention.

FIG. 3A illustrates the ability of the select Mas receptor antagonists, A779, ($C_{39}H_{60}N_{12}O_{11}$) which is known to block native Ang-(1-7) NO production, to also block NO production induced by the oligopeptide of the invention, namely PN-A5. In these studies, HUVEC cells were incubated with DAF-FM, 1 µM to measure real-time NO production. Cells were treated with either PN-A5 alone (1.0 mM, n=10), PN-A5+A779 (n=6). Measurements were obtained using an Olympus 550 Confocal Microscope and analyzed using Image J. Images were obtained every 10 sec. These results indicate that the oligopeptide PN-A5 actions are due to activation of the Mas receptor.

Figure 3B:
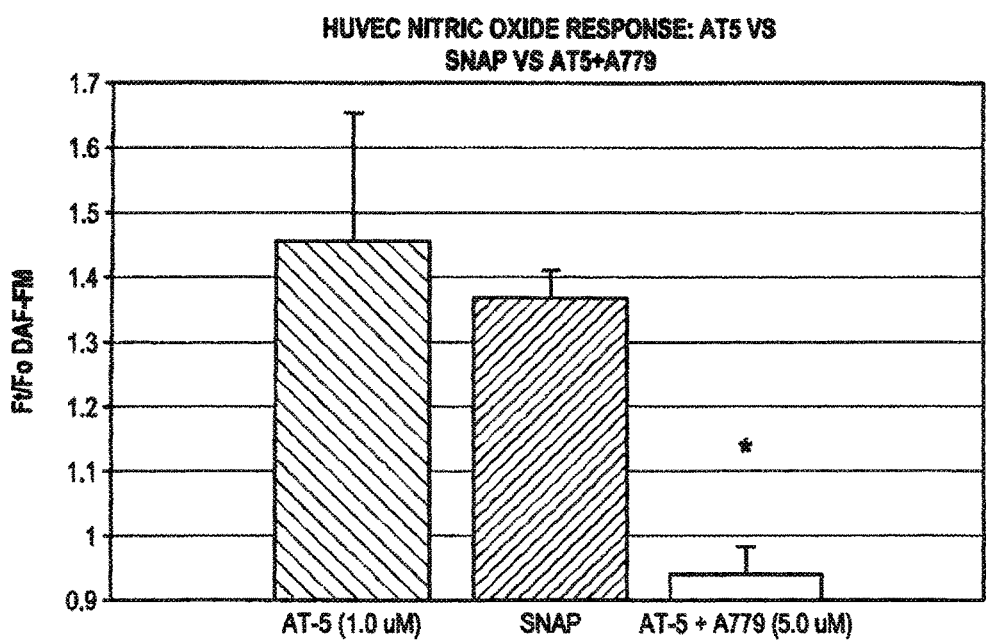
FIG. 3B is a graph showing the averaged effect of the select Mas receptor antagonists A779 on NO production induced by oligopeptide PN-A5.

FIG. 3B shows the averaged effect of the select Mas receptor antagonists, A779, which is known to block native Ang-(1-7) NO production, to also block NO production induced by the oligopeptide of the invention, PN-A5. In these studies, HUVEC cells were incubated with DAF-FM, 1 µM to measure real-time NO production. Cells were treated with either PN-A5 alone (1.0 mM, n=10), PN-A5+A779 (n=6), or the NO donor S-nitroso-N-acetylpenicillamine (SNAP). Fluorescent measurements were obtained using an Olympus 550 Confocal Microscope and analyzed using Image J. Images were obtained every 10 sec. The NO response produced by PN-A5 was completely blocked by A779 demonstrating that PN-A5's ability to increase NO is due to PN-A5 actions on the Mas receptor.

Example 2

Effects of Ang-(1-7) Derivative on Heart Failure (HF) Induced Cognitive Impairment A total of 33, male C57Bl/6J adult mice (Harlan, 8-10 weeks old) were used. Mice were randomly assigned to either the sham (n=12) or congestive heart failure (CHF) group (n=21). Experimental groups are described as follows: sham+saline, CHF+saline, CHF+PN-A5. All mice prior to surgery were weighed and anesthetized. For the CHF mice, MI was induced by ligation of the left coronary artery (LCA). Under anesthesia (2.5% isoflurane in a mixture of air and 02) a thoracotomy was performed at the fourth left intercostal space and the LCA permanently ligated to induce a myocardial infarction (MI). Occlusion of the LCA was confirmed by observing blanching, a slight change in color of the anterior wall of the left ventricle downstream of the ligature. Sham mice underwent the same procedure with the exception of ligating the LCA.

Following 8 weeks post MI surgery, CHF mice were treated with either daily subcutaneous injections of the Ang-(1-7) derivative PN-A5 (1 mg/kg/day) for 28 days or saline. After 21 days, animals were tested for object recognition using a standard NOR test as described below. After approximately 25 days of treatment, animals were tested for spatial memory using the standard Morris water task as described below.

Novel Object Recognition (NOR): The apparatus consisted of an evenly illuminated Plexiglas box (12 cm×12 cm×12 cm) placed on a table inside an isolated observation room. All walls of the apparatus were covered in black plastic, and the floor was grey with a grid that was used to ensure that the location of objects did not change between object familiarization and test phases. The mouse behavior and exploration of objects was recorded with a digital camera. The digital image from the camera was fed into a computer in the adjacent room. Two digital stopwatches were used to track the time the mouse spent interacting with the objects of the test. All data was downloaded to Excel files for analysis. Triplicate sets of distinctly different objects were used for the test.

The novel object recognition task included 3 phases: habituation phase, familiarization phase, and test phase. For the habituation phase, on the first and second day, mice were brought to the observation room habituated to the empty box for 10 min per day. On the third day, each mouse had a "familiarization" trial with two identical objects followed by a predetermined delay period and then a "test" trial in which one object was identical to the one in the familiarization phase, and the other was novel. All stimuli were available in triplicate copies of each other so that no object needed to be presented twice. Objects were made of glass, plastic or wood that varied in shape, color, and size. Therefore, different sets of objects were texturally and visually unique. Each mouse was placed into the box the same way for each phase, facing the center of the wall opposite to the objects. To preclude the existence of olfactory cues, the entire box and objects were always thoroughly cleaned with 70% ethanol after each trial and between mice. During the familiarization phase, mice were allowed to explore the two identical objects for 4 min and then returned to their home cages. After a 2 hour delay, the "test phase" commenced. The mice were placed back to the same box, where one of the two identical objects presented in the familiarization phase was switched to a novel one and the mouse was allowed to explore these objects for another 4 min. Mouse "exploratory behavior" was defined as the animal directing its nose toward the object at a distance of ~2 cm or less. Any other behavior, such as resting against the object, or rearing on the object was not considered to be exploration. Exploration was scored by an observer blind to the mouse's surgical group (CHF vs. Sham). Finally, the positions of the objects in the test phases, and the objects used as novel or familiar, were counterbalanced between the 2 groups of mice.

Discrimination ratios were calculated from the time spent exploring the novel object minus time spent exploring the familiar object during the test phase divided by the total exploration time. DRatio=(t novel−t familiar)/(t novel+t familiar). Data were analyzed from first 2 minutes of 'test phase'. A positive score indicates more time spent with the novel object, a negative score indicates more time spent with the familiar object, and a zero score indicates a null preference. All NOR data was examined using one-way analysis of variance, between subjects (ANOVA). Individual group differences were tested using the post hoc Tukey HSD test. In comparisons between groups of different sample sizes, equal variance was tested using a modified Levene's test. All statistical tests and p-values were calculated using MS Excel with Daniel's XLtoolbox and alpha was set at the 0.05 level. Error bars represent SEM.

Morris Water Task: Testing Spatial Learning and Memory/Visual Test: The apparatus used was a large circular pool approximately 1.5 meters in diameter, containing water at 25° C. made opaque with addition of non-toxic white Crayola paint. An escape platform was hidden just below the surface of the water. Visual, high contrast cues were placed on the walls of the test room. A digital camera connected to a computer in the adjacent room is suspended over the tank to record task progress. For spatial testing prior to MI at 4 and 8 weeks post-MI or sham surgery, the platform was located at different sites in the pool.

During the spatial version of the Morris water task, all animals were given 6 training trials per day over 4 consecutive days. During these trials, an escape platform was hidden below the surface of water. Mice were released from seven different start locations around the perimeter of the tank, and each animal performed two successive trials before the next mouse was tested. The order of the release locations was pseudo-randomized for each mouse such that no mouse was released from the same location on two consecutive trials. Performance on the swim task was analyzed with a commercial software application (ANY-maze, Wood Dale, Ill.). Because different release locations and differences in swimming velocity produce variability in the latency to reach the escape platform, a corrected integrated path length (CIPL) was calculated to ensure comparability of mice performance across different release locations. The CIPL value measures the cumulative distance over time from the escape platform corrected by an animal's swimming velocity, and is equivalent to the cumulative search error. Therefore, regardless of the release location, if the mouse mostly swims towards the escape platform the CIPL value will be low. In contrast, the more time a mouse spends swimming in directions away from the platform, the higher the CIPL value.

Figure 4:
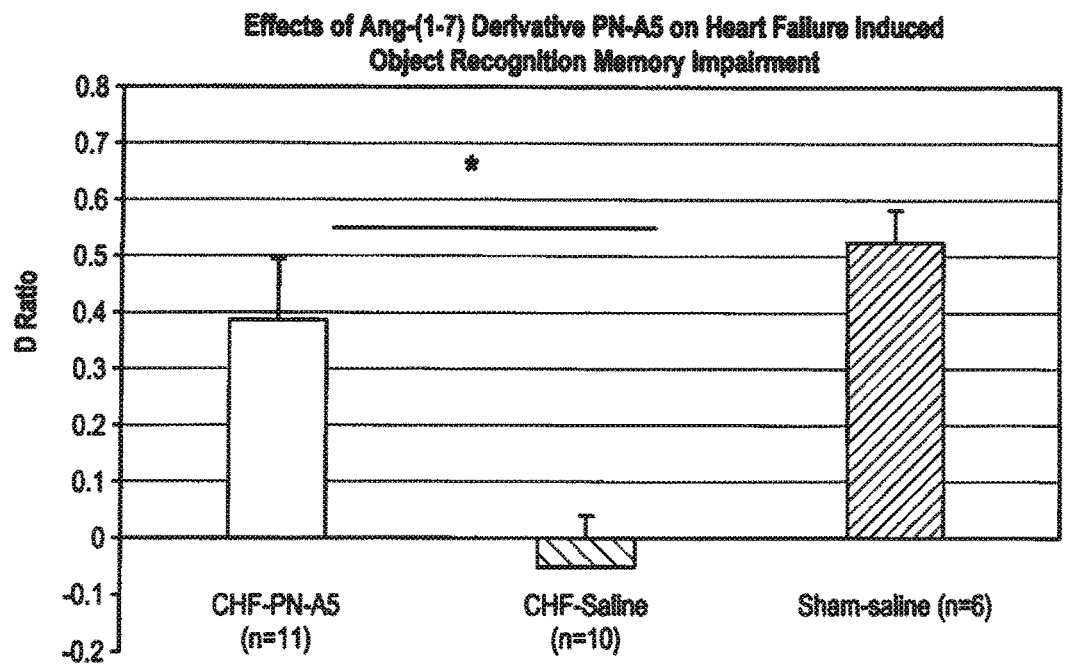
FIG. 4 is a graph showing the effects of oligopeptide PN-A5 on heart failure induced object recognition memory impairment.

Following approximately 21 days of treatment with oligopeptide PN-A5, CHF mice showed object recognition memory improvement. FIG. 4 illustrates the effects of three weeks treatment with oligopeptide PN-A5 on object recognition memory as determined by the Novel Object Recognition Test (NOR). The mean performance of CHF mice with oligopeptide PN-A5 treatment (n=11) was similar to sham mice with saline (n=6), (CHF-Ang-(1-7) derivative PN-A5 M=+0.38, SE 0.11 vs. Sham-saline M=+0.52, SE 0.06) and significantly greater in comparison to CHF mice treated with saline (n=10) (M=−0.05, SE 0.09, *=p=0.009. These results demonstrate that oligopeptide PN-A5 acts to attenuate and even rescue object recognition memory impairment in mice with CHF.

Figure 5:
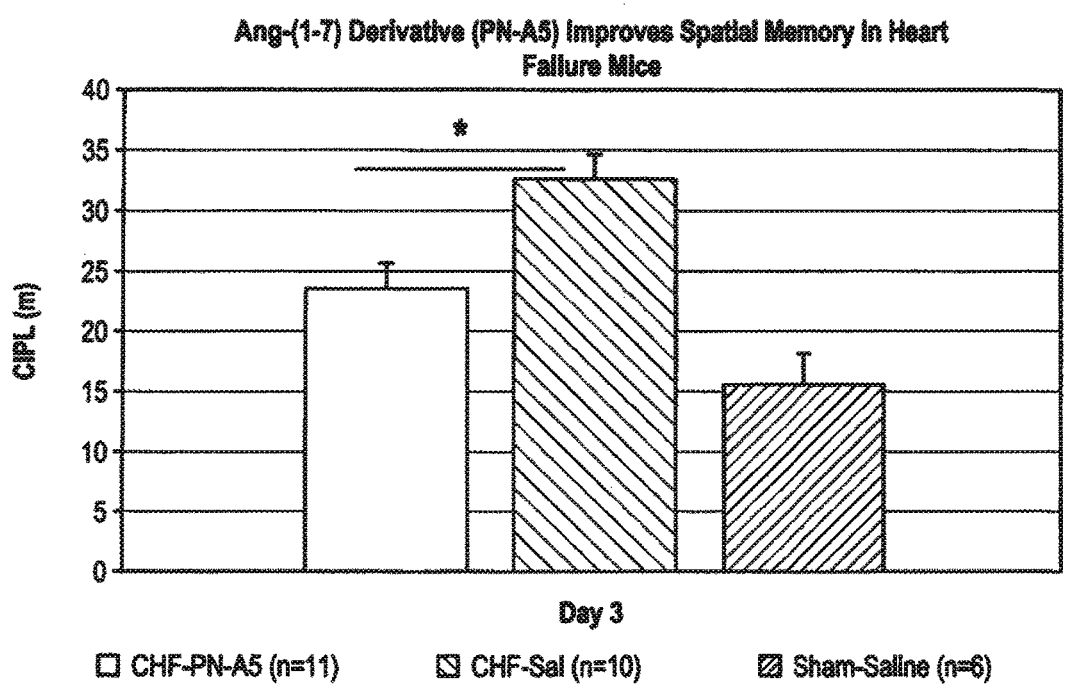
FIG. 5 is a graph showing the effects of oligopeptide PN-A5 on heart failure induced spatial memory impairment.

Following approximately 25 days of treatment with oligopeptide PN-A5, CHF mice showed spatial memory improvement. FIG. 5 shows the mean CIPL of CHF+ oligopeptide PN-A5 mice (n=11), CHF-saline treated mice (n=10) and Sham+saline mice (n=6). The CHF+oligopeptide PN-A5 mice showed significant improvement in spatial memory day 3 of the Morris swim task as compared to CHF-saline mice. CHF mice treated with saline had a significantly higher CIPL score as compared to CHF-oligopeptide PN-A5 treated mice (CHF-saline M=32.5, SE=2.1 vs CHF-oligopeptide PN-A5 M=23.5, SE 2.2, *=p=0.003. These results demonstrate that oligopeptide PN-A5 improves spatial memory.

Example 3

Effect of Oligopeptide PN-A5 on Nitric Oxide
Bone Pain

Female BALB/cfC3H mice (Harlan, Ind., USA) were 15 to 20 g prior to initiation of study (n=5 animals per treatment group). Clinical signs of morbidity were monitored and mice not meeting inclusion parameters (e.g. paralysis, rapid weight loss of >20% in 1 week) were removed from the study.

Mice were anesthetized with ketamine:xylazine (80 mg: 12 mg/kg, 10 ml/kg injection volume; Sigma-Aldrich). An arthrotomy was performed. The condyles of the right distal femoris were exposed and a hole was drilled in to create a space for injection of $4 \times 10^4$ 66.1 cells in 5 µL Opti-MEM or 5 µL Opti-MEM without cells in control animals within the intramedullary space of the mouse femoris. Injections were made with an injection cannula affixed via plastic tubing to a 10-4 Hamilton syringe (CI31, Plastics One). Proper placement of the injector was confirmed through use of Faxitron X-ray imaging. Holes were sealed with bone cement.

Spontaneous pain (flinching and guarding), and tactile allodynia were measured 0, 15, 30, 60, 90 and 120 minutes after a single dose of drug was administrated in a blinded fashion on Day 7. Breast cancer-induced hypersensitivity returned to baseline levels 2 hours after drug administration. Flinching and guarding were observed for duration of 2 minutes during a resting state. Flinching was characterized by the lifting and rapid flexing of the right hind paw when not associated with walking or movement. Flinches were recorded on a five-channel counter. Guarding was characterized by the lifting the right hind limb into a fully retracted position under the torso. Time spent guarding over the duration of 2 minutes was recorded.

The assessment of tactile allodynia consisted of measuring the withdrawal threshold of the paw ipsilateral to the site of tumor inoculation in response to probing with a series of calibrated von Frey filaments using the Chaplan up-down method with the experimenter blinded to treatment groups. The 50% paw withdrawal threshold was determined by the nonparametric method of Dixon.

On day 7, mice received an intraperitoneal (i.p.) injection of either saline or 0.8 µg/µL (200 µL) for a total dose of 800 µg/kg. The in-vivo efficacy of PN-A5 was measured for a total of 2 hours.

Within group data were analyzed by non-parametric one-way analysis of variance. Differences were considered to be significant if P≤0.05. All data were plotted in GraphPad Prism 6.

Figure 6A:
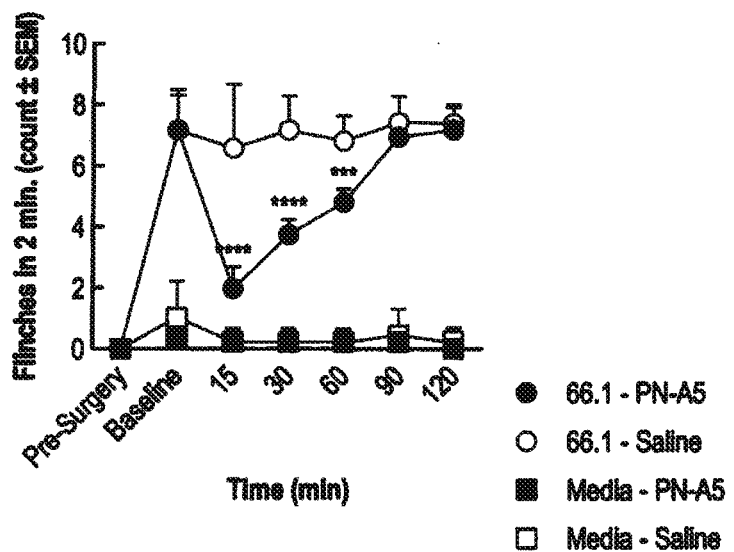
FIG. 6A is a graph showing oligopeptide PN-A5 attenuates spontaneous pain in CIBP acutely.
Figure 6B:
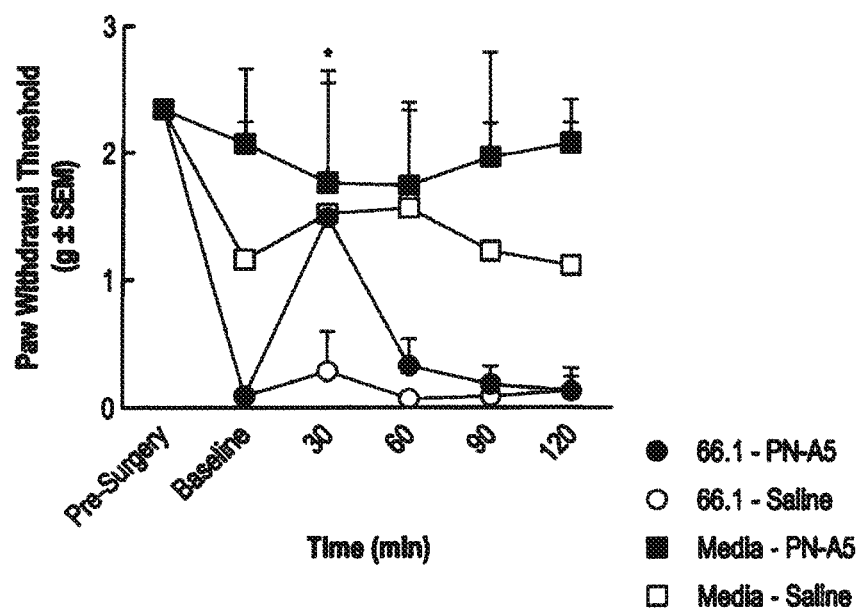
FIG. 6B is a graph showing the results of tactile allodynia test using von Frey filaments.

FIG. 6 shows the results on the effects of oligopeptide PN-A5 on cancer induced bone pain (CIBP). Cancer implanted into the distal femoralis of mice induced a significant increase in the number of spontaneous flinches (FIG. 6A) and time spent guarding (FIG. 6B) after 7 days. Administration of a bolus of PN-A5 (800 µg/kg, i.p.) significantly reversed cancer induces spontaneous pain for nearly one hour in duration (flinching: 60 min; guarding: 30 min; p<0.001). Similarly, cancer-induced tactile hypersensitivity was significantly attenuated 30 minutes after injection (p<0.01). For all measurements, the time of peak effect was 15-30 min. Behaviors returned to post-surgery values 90 min post-injection. Media inoculated, sham control animals did were not statistically different from pre-surgery baselines at any point during time-course.

Example 4

Effect of Ang(1-7) on Cancer-Induced Bone Pain

The effect on cancer-induced bone pain of the archetypical Mas receptor agonist, native Ang(1-7) was investigated. It was discovered that the action of Ang-(1-7) at the Mas receptor inhibits pain via the tumor-nociceptor microenvironment and not the tumor-bone environment because Ang-(1-7) induced analgesia but did not significantly change the tumor-induced degradation of the bone or otherwise reduce bone loss. Chronic treatment with Ang-(1-7) did not significantly alter tumor proliferation, further suggesting the analgesic effect is directly towards inhibiting nociceptive activation and not due to changes in tumor burden.

Cell Culture: A murine mammary adenocarcinoma cell line, 66.1, was cultured in Eagle's minimum essential medium with 10% fetal bovine serum, 100 IU-1 penicillin, and 100 µg mL-1 streptomycin (P/S). The 66.1 cells were plated in T-75 tissue culture flasks, allowed to grow exponentially in an incubator at 37° C. and 5% $CO_2$. The viability of cells cultured with treatments described below was measured using the XTT assay (ATCC, Manassas, Va.).

Animals: Female BALB/cAnNHsd mice (Harlan, Ind., USA) between 15 and 20 g were used in this study. Mice were housed in a climate control room on a 12-hour light/dark cycle and allowed food and water ad libitum. Animals were monitored on days 0, 7, 10, and 14 of the study for clinical signs of rapid weight loss and signs of distress.

Drug Treatment: Animals received Angiotensin-(1-7) (Tocris, Ellisville, Mo.), the MasR antagonist A-779 (Abcam, Cambridge, Mass.), the AT1 antagonist Losartan potassium (Tocris Bioscience, Minneapolis, Minn.), or the AT2 antagonist PD 123319 ditrifluoroacetate (Tocris Bioscience, Minneapolis, Minn.) dissolved in 0.9% saline. All intraperitoneal (i.p.) injections were made at a volume of 10 mL/kg. Systemic doses as follows: Ang-(1-7)=0-100 µg/kg, A-779=0.19 µg/kg, Losartan potassium=0.4 mg/kg, PD 123319 ditrifluoroacetate=0.4 mg/kg. In antagonist studies, A-779, Losartan potassium, or PD 123319 ditrifluoroacetate was administered 30 minutes prior to Ang-(1-7).

Tail Flick: A warm water (52° C.) tail flick test was used to determine the effects of Ang-(1-7) on acute nociception. The distal third of the tails of naïve mice were submerged into the water bath. The withdraw latency, defined as the time for the tail to be withdrawn from the water bath, was recorded. A cutoff time of 10 seconds was enforced to prevent tissue damage. Baseline latencies were recorded prior to drug administration. Animals were dosed (i.p.) with Ang-(1-7) (0-100 µg/kg). Tail flick latencies were reassessed 15, 30, 60, 90, 120, 150, and 180 minutes post-treatment.

Rotarod: A rotarod performance test was used to determine the motor and/or sedative effects of Ang-(1-7) (Rotamex 4/8, Columbus Instruments, Columbus, Ohio, USA). Three days prior to testing, naïve mice were subjected to 5 trials in which they were able to acclimate to the rotating rod (10 revolutions/min). On the day of testing, animals were allowed one trial and then baselined. The amount of time the animal remained on the rod was recorded, with a cutoff time of 120 seconds to prevent exhaustion. Animals were dosed (i.p.) as previously described and reevaluated 15, 30, 60, and 120 minutes post-administration.

Arthrotomy—Intramedullary Implantation of 66.1 Cells: To induce CIBP, an arthrotomy was performed. Briefly, animals were anesthetized with 80 mg/kg ketamine-12 mg/kg xylazine (in a 10 mL/kg volume). The surgical area was shaved and cleaned with 70% ethanol and betadine. The condyles of the right femur were exposed and a burr-hole (0.66 mm) was drilled to create a space for the 66.1 cell inoculation. A 5 µl volume of 66.1 cells (8,000 cells per 1 µl) in MEM (or 5 µl MEM without cells in sham animals) was injected into the intramedullary space of the mouse femora. Proper placement of the injector was confirmed by radiograph (Faxitron X-ray imaging). Holes were sealed with bone cement and the patella reset. Muscle and skin were closed in separate layers with 5-0 vicryl suture and wound autoclips, respectively. Animals were given 8 mg/kg (10 mL/kg volume) gentamicin to prevent infection. Staples were removed 7 days post-surgery.

Acute Behavioral Testing: Fourteen days post-surgery, baseline behaviors of spontaneous flinching/guarding were recorded. Flinching was characterized by the lifting and rapid flexing of the hind paw ipsilateral to femoral inoculation when not associated with walking or other movement. Guarding was characterized by the lifting the inoculated hind limb into a fully retracted position under the torso. The total number of flinches and the time spent guarding 2 min duration was recorded. Mice were then separated into treatment groups and dosed systemically with Ang-(1-7) (0-10 µg/kg), A-779 (0.19 µg/kg), Losartan potassium (0.4 mg/kg), PD 123319 (0.4 mg/kg), vehicle (0.9% saline), or a combination of Ang(1-7) and each antagonist. Antagonists were administered 30 minutes prior to Ang-(1-7). Following administration, animals were tested at over a three-hour time course until their pain behaviors returned to baseline Chronic Behavioral Testing: Seven days post-surgery, baseline behaviors of spontaneous pain, as described above, were recorded. Mice were treated (i.p.) with Ang-(1-7) (0.058 µg/kg), A-779 (0.19 µg/kg), vehicle (0.9% saline), or a combination. Antagonist was administered 30 minutes prior to Ang-(1-7). Animals were dosed at the same time each day 7 to 14 days post-surgery. On day 10, pain behaviors were assessed 15 minutes following treatment, based on the time of peak effect determined by the acute studies. Fourteen days post-surgery, behaviors were again recorded pre- and post-treatment. Animals were sacrificed following treatment and testing on the fourteenth day post-surgery, and the following tissues were collected for biochemical analyses: serum, femur extrudate, and lumbar dorsal root ganglia.

Nesting: Nesting behaviors of naïve, media, and cancer-inoculated mice were assessed using the protocol described by Negus et al. Animals were acclimated to individual cages, without an existing nest, for 30 minutes prior to drug administration. Cotton fiber nestlets were cut into 6 equal pieces, and each piece was placed in the cage in 6 zones in the manner previously described following drug administration. Throughout the duration of the 100-minute time course, the number of cleared zones was recorded; upon completion the height (mm) of each fluffed nestlet was measured.

Western Blot Analysis: Dorsal root ganglia (DRG) and femur extrudates from mice used in behavioral studies were analyzed for expression of MasR. DRGs were homogenized in modified radioimmunoprecipitation assay (RIPA) buffer with protease inhibitor cocktail and EDTA (Pierce, Rockford, Ill., USA) via sonication. 10 µg of each sample was resolved on a 10% SDS-polyacrylamide gels (TGX Criterion XT; Bio-Rad, Hercules, Calif.) and transferred to a polyvinylidene difluoride membrane (PVDF, Bio-Rad, Hercules, Calif.). Ipsilateral and contralateral femurs were removed from each animal. For each femur, the proximal and distal ends were clipped and the intramedullary extrudate was flushed six times with 700 µL phosphate-buffered saline containing protease inhibitor cocktail and EDTA (Pierce, Rockford, Ill., USA). Femur marrow from five animals was pooled per sample and 15 µg of sample was resolved and transferred in the same manner as DRGs. Protein transfer was verified by staining blots with Ponceau S (Sigma, St. Louis, Mo.), and PVDF membranes were blocked with 5% non-fat dry milk in Tris-buffered saline containing 0.05% (v/v) Tween-20 (TBST) for one hour at room temperature. Membranes were then incubated with primary antibody:rabbit polyclonal anti-Angiotensin-(1-7) Mas Receptor (Alomone Labs AAR-013; 1:200 dilution for DRGs or 1:800 for femurs) or mouse monoclonal anti-actin AC40 (Cell Signaling 7076S; 1:4,000 dilution) in 1% milk in TBST overnight at 4° C. The membranes were washed in TBST and incubated with appropriate secondary antibodies (Cell Signaling 7074 Anti-rabbit IgG HRP-Linked, 1:10,000 dilution; Cell Signaling 7076 Anti-mouse IgG HRP-Linked, 1:5000 dilution) for 1 hour at room temperature. Membranes were again washed and developed using enhanced chemiluminescence (Clarity ECL Substrate, Bio-Rad, Hercules, Calif.), and bands were detected using GeneMate Blue-Ultra Autorad films (BioExpress, Kaysville, Utah. Bands were quantitated and corrected for background using ImageJ densitometric software (Wayne Rasband, Research Services Branch, National Institute of Mental Health, Bethesda, Md.). All data were normalized to actin in each lane and reported as fold change over untreated control.

Ang-(1-7) Administration in Established CIBP Attenuates Spontaneous Pain in a MasR Dependent Manner.

Figure 7A:
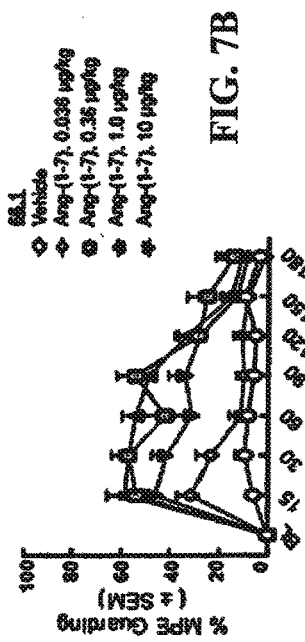
FIGS. 7A-7F is a series of graphs showing the pain responses (guarding and flinching) of mice having a bone intramedullary transplantation of a breast cancer cell line under various single-dose therapeutic treatment regimens and the blockade by the Mas receptor antagonist A779.

The antinociceptive efficacy of Ang-(1-7) in a model of established CIBP in which 66.1 tumor cells were injected into the right femurs of syngeneic BALB/cAnNHsd mice was investigated. Prior to surgery, mice did not display behavioral signs of pain (data not shown). Animals showed a significant amount of flinching (FIG. 7A at "post-Sx") and guarding (FIG. 7B at "post-Sx") compared to media-treated controls ($p<0.0001$, n=8). A single systemic injection of Ang-(1-7) (0.036, 0.360, 1, and 10 µg/kg) or vehicle was administered, and pain behaviors were assessed. Animals given an acute i.p. administration of Ang-(1-7) showed a significant ($p<0.01$, n=8) reduction in spontaneous pain behaviors with an onset 15 min after injection of either 0.36 or 1 µg/kg which persisted for nearly 2 hours (FIGS. 7A and 7C).

Figure 7B:
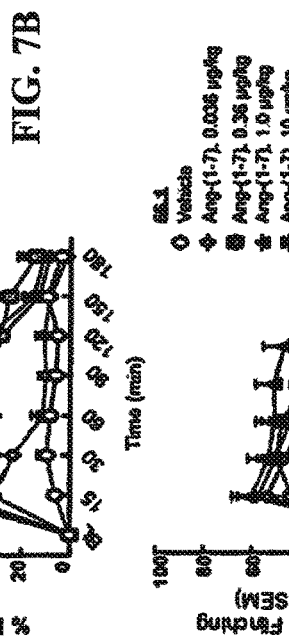
Figure 7C:
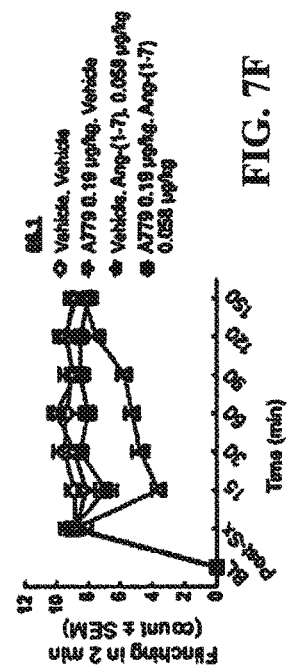
Figure 7D:
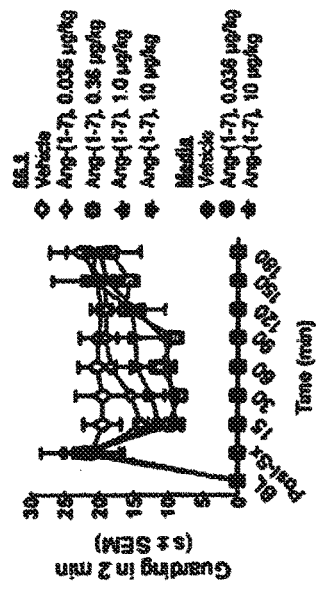

Dose response curves were constructed from data collected at the time of peak effect, 15 min, for guarding and flinching behavior (FIGS. 7B and 7D, respectively). At 15 min, the maximum effect of Ang-(1-7) in reducing guarding behavior was 52.75% ($p<0.01$, n=8) with a corresponding A90 dose of 0.058 µg/kg (FIG. 1B). Flinching displayed less of a dose-dependency and a more significant inhibition at the lower dose (0.036 µg/kg). Thus, a single injection of Ang-(1-7) is effective in reducing spontaneous pain behavior by more than 50% in animals with established CIBP.

Figure 7E:
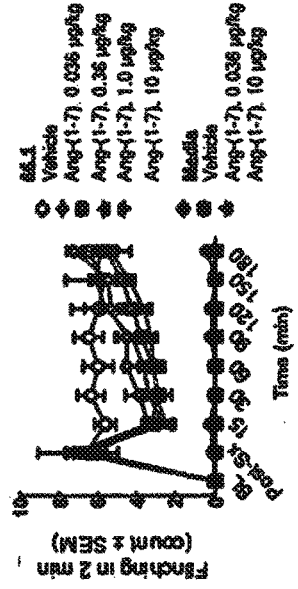
Figure 7F:
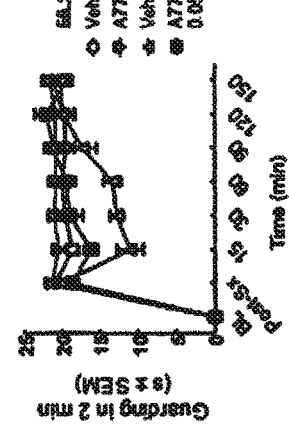

To confirm that the observed Ang-(1-7) effect is mediated by the Mas receptor, A-779 (0.19 µg/kg), a selective MasR antagonist, or vehicle was administered 30 minutes prior to Ang-(1-7) (0.058 µg/kg) 14 days post-femur inoculation. Inhibition of MasR with A-779 alone did not alter spontaneous or evoked pain thresholds; however, pretreatment with A-779 significantly inhibited Ang-(1-7) attenuation of guarding (FIG. 7E, $p<0.01$) and flinching (FIG. 7F, $p<0.001$). These data demonstrate that Ang-(1-7) elicits antinociception in established CIBP through actions at MasR.

Antinociceptive Effects of Ang-(1-7) Through MasR are Maintained after Repeated Administration.

Figure 8B:
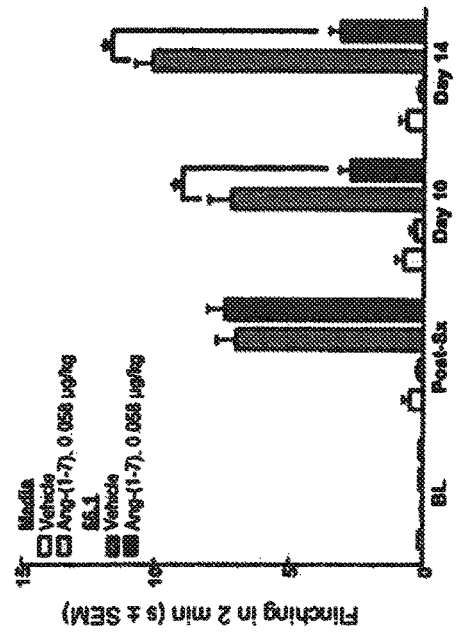
FIGS. 8A-8D is a series of bar graphs showing the pain responses (guarding and flinching) of mice having a bone intramedullary transplantation of a breast cancer cell line under various chronic therapeutic treatment regimens and the blockade by the Mas receptor antagonist A779.

The antinociceptive activity of repeated Ang-(1-7) was investigated to determine whether, like other analgesics, chronic administration results tolerance. Ang-(1-7) (0.058 µg/kg, i.p.) was administered daily, beginning 7 days post implantation of 66.1 cells into the femur. Mice were evaluated for CIBP spontaneous pain behaviors on day 7 prior to drug administration, and on days 10 and 14 post-surgery 15 minutes post-treatment. Cancer inoculation significantly increased the amount of time spent guarding and number of flinches 7 days post-surgery ($p<0.0001$, n=12). Animals experienced significant ($p<0.0001$, n=12) reduction in guarding (FIG. 8A) and flinching (FIG. 8B) following Ang-(1-7) treatment on days 10 and 14 post-surgery. Vehicle treatment had no significant effect.

Figure 8D:
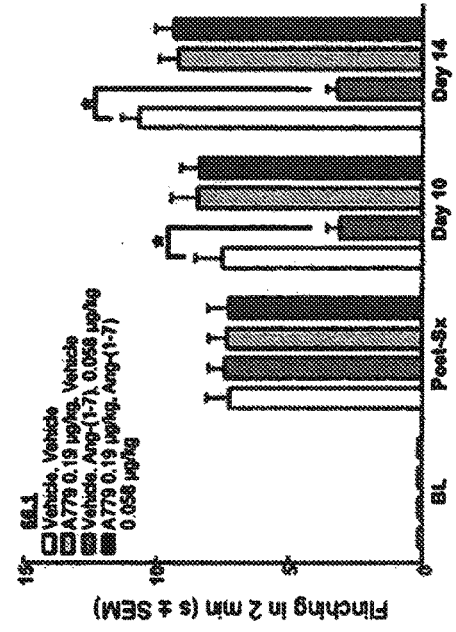
Figure 8A:
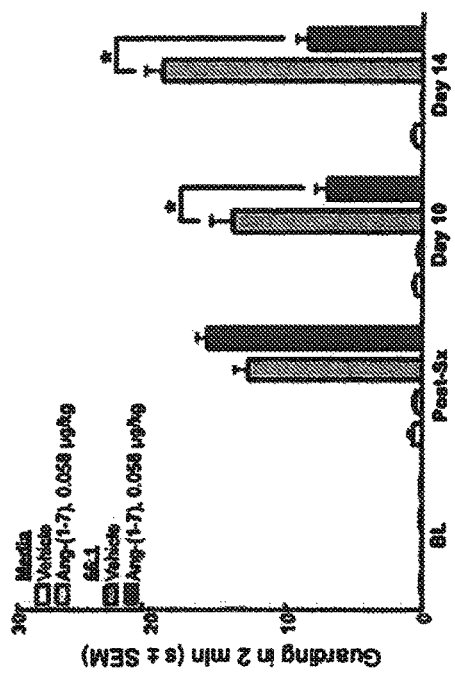
Figure 8C:
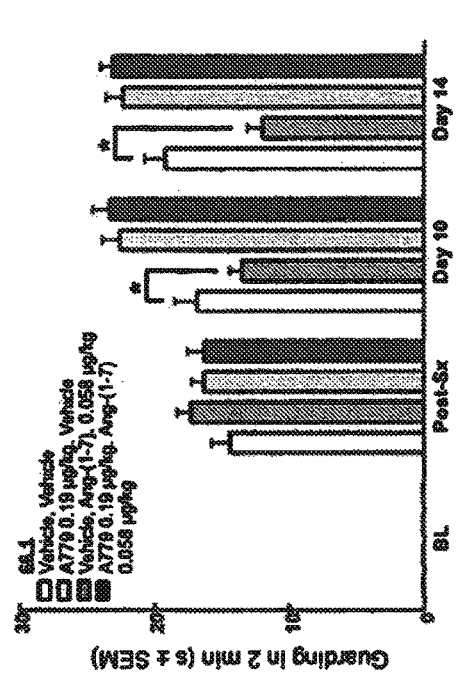

A-779 was again used to confirm that the antinociceptive effects of Ang-(1-7) are mediated by the Mas receptor. A-779 (0.19 µg/kg) was administered 30 minutes prior to Ang-(1-7) (0.058 µg/kg) daily 7-14 days post-cancer inoculation (FIGS. 8C and 8D). Administration of A-779 alone had neither a pro- or anti-nociceptive effect on the mice, and similar to earlier observations following a single injection, the chronic pre-treatment with A779 before Ang-(1-7) prevented attenuation of CIBP by the latter.

Effects of AT1/AT2 Antagonists on Ang-(1-7)/MasR-Mediated Antinociception in Established CIBP.

Figure 9B:
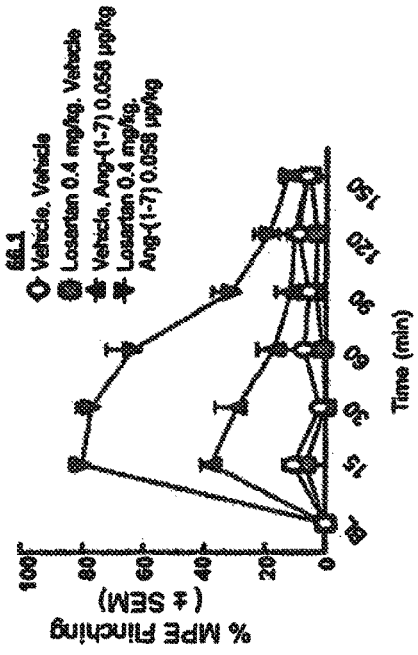
FIGS. 9A-D is a series of graphs showing the pain responses of mice having an intramedullary transplantation of a breast cancer cell line under various chronic treatment regimens using either Ang-(1-7) or antagonists of the AT1 or AT2 receptor.
Figure 9D:
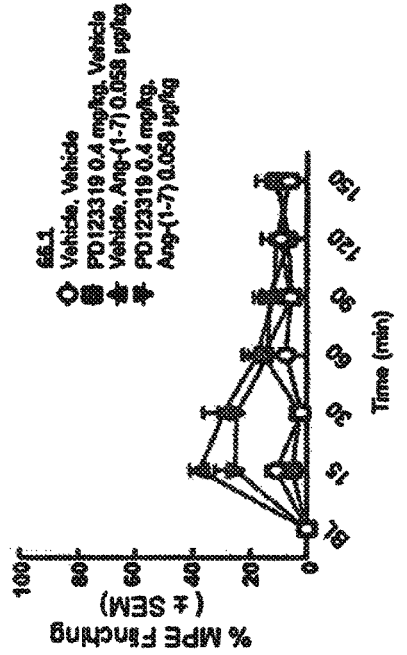
Figure 9A:
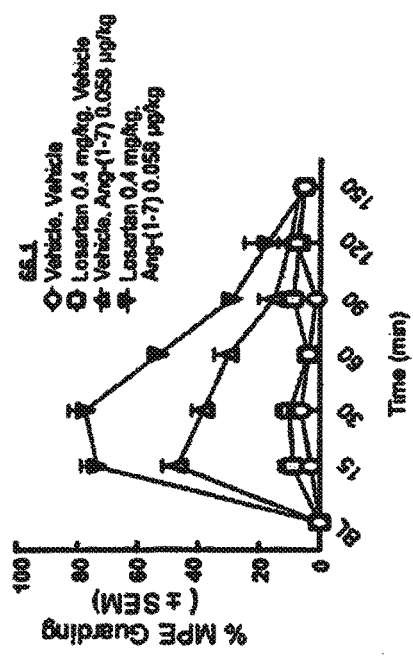
Figure 9C:
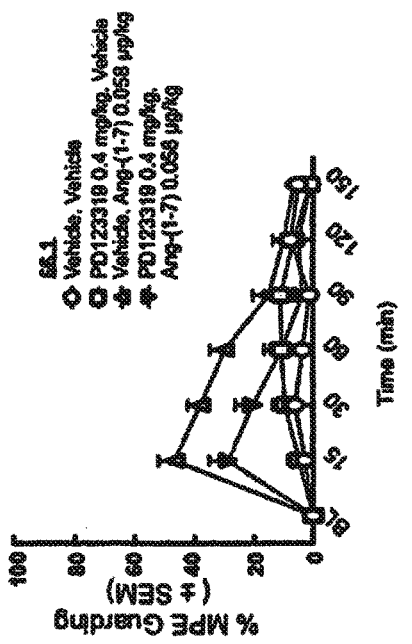

Ang II is the precursor molecule to Ang-(1-7). Accordingly, the role of the AngII receptors in mediating Ang-(1-7) antinociception was investigated using a pre-treatment of the AT1 or AT2 selective antagonists, Losartan potassium (Ki=10 nM) and PD 123319 (also known as EMA200) (IC50=34 nM), respectively. Animals were inoculated with 66.1 cells or media, as previously described, and pain behaviors were assessed 14 days post-femur inoculation. Mice received either the AT1 or AT2 antagonist (0.4 mg/kg, i.p.) 30 minutes prior to Ang-(1-7) (0.058 µg/kg, i.p.), or vehicle (0.9% saline). Spontaneous pain behaviors of flinching and guarding were recorded 15, 30, 60, 90, 120, and 150 minutes post-administration. Confirming the previous results, Ang-(1-7) administration alone reduced pain behaviors (p<0.01, n=7), while neither Losartan potassium nor PD 123319 significantly altered pain behaviors when administered alone. Interestingly, administration of the AT1 receptor antagonist, Losartan potassium, prior to Ang-(1-7) yielded a 77.527% maximal possible efficacy (MPE) in reducing guarding (p<0.0001, n=7) 30 minutes post-administration (FIG. 9A) and an 80.56% MPE in reducing flinching (p<0.0001, n=7) 15 minutes post-administration (FIG. 9B). However, use of the AT2 antagonist, PD 123319, prior to Ang-(1-7) did not further increase nor decrease guarding or flinching of animals with established CIBP (FIGS. 9C and 9D) as compared to the animal group treated with solely Ang-(1-7). The additive effect of Losartan potassium to potentiate Ang-(1-7)-induced antinociception was not further investigated but may result from the ability of Losartan to prevent Ang-(1-7) binding to the AT1 receptor, thereby increasing the free concentration of Ang-(1-7) to bind to the Mas receptor.

Ang-(1-7) Administration in Established CIBP does not Change Nesting Behaviors.

Figure 10B:
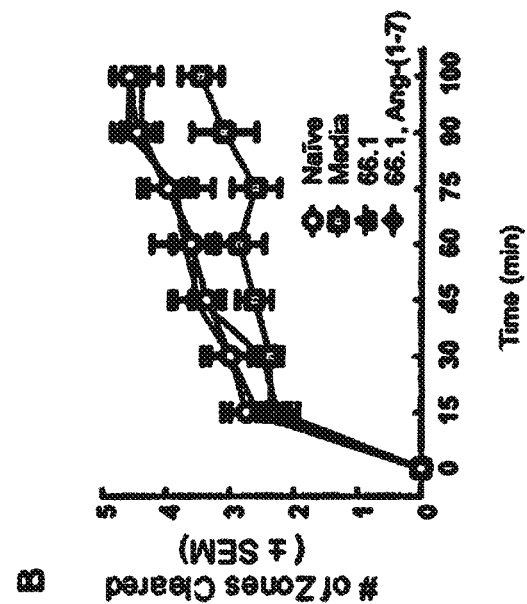
FIGS. 10A-10B is a series of graphs showing the nesting behavior of experimental mice with or without bone cancer under various treatment regimens.
Figure 10A:
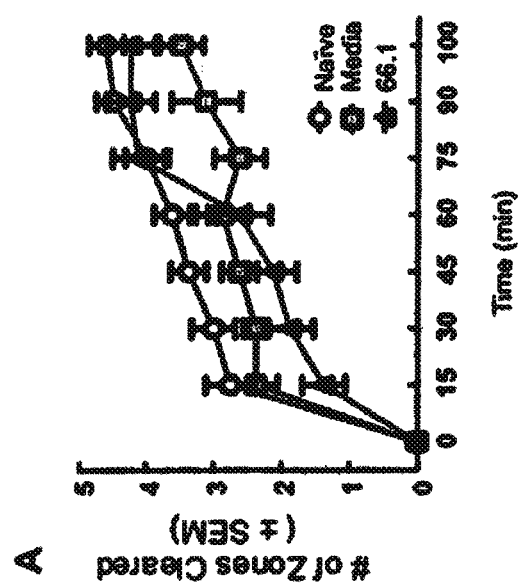

Nesting is an innate behavior in mice that is hindered by various states of pain. The effect of both the arthrotomy and Ang-(1-7) administration on nesting behavior was evaluated. Six equally sized pieces of nestlet were placed into 6 zones of the animals' individual cages. The number of zones that the animals cleared of the nestlet pieces was recorded over the 100-minute time course (FIG. 10A). During the first hour of the study on post-surgical day 6, the 66.1-inoculated animals cleared significantly fewer zones than the naïve animals (p<0.05). After the second hour of the study, the media animals cleared fewer zones than both the naïve and 66.1-inoculated animals (p<0.05). A second study was conducted on post-surgical day 15 in which 66.1-inoculated animals were treated with Ang-(1-7) (0.058 µg/kg, i.p.) or vehicle (0.9% saline) (FIG. 10B). The nesting behaviors of both treated cancerous groups did not differ significantly from the naïve group. However, at both the 75 and 90-minute time points, the media animals cleared fewer zones than the other groups (p<0.05). These data demonstrate that while the nesting of animals with established CIBP alters the nesting behaviors of mice, Ang-(1-7) administration does not further alter these complex behaviors.

Ang-(1-7) Administration Results in Antinociception but not Motor Impairment in Naïve Mice Ang-(1-7) was systemically administered (0.360, 1, 10 µg/kg, i.p.) to naïve mice. Small but significant increase in thermal tail flick latencies were observed (data not shown). Ang-(1-7) effects peaked between 15 and 30 min post administration with 1 µg/kg Ang-(1-7) (MPE=27.8%, p<0.001) and 10 µg/kg Ang-(1-7) (MPE=20.2%, p<0.01) that returned to baseline between 90 to 120 min.

To exclude the possibility that Ang-(1-7) administration reduced mobility in order to increase tail withdraw latency, rotarod testing was performed. Naïve animals were trained to walk on a rotating rod for 2 min. After training, animals were injected with Ang-(1-7) by either spinal (0.3 pmol/5 µL) or systemic routes (0.058 and 10 µg/kg). No significant differences in rotarod latencies were observed between vehicle and Ang-(1-7) treated mice (results not shown; p=0.99 i.t.; p=0.18 i.p.). Together, these data suggest that systemic Ang-(1-7) is antinociceptive after a single administration without noticeable impact on motility.

MasR is Expressed in the Dorsal Root Ganglion and Femur Extrudate.

Ipsilateral lumbar dorsal root ganglion (DRG) and femur extrudate were collected from naive, sham, cancer (66.1), and 66.1 Ang-(1-7) treated mice. In naïve mice, MasR is expressed in the dorsal root ganglia (FIG. 11A); MasR bands were observed at ~50 kDa and ~40 kDa. Sham surgery (i.e. media only) or the introduction of the murine mammary adenocarcinoma line 66.1 into the femoral intramedullary space did not significantly alter MasR expression levels in ipsilateral DRGs relative to the contralateral control DRGs (FIG. 11B). MasR was also found to be expressed in the femur extrudates of the same mice (FIG. 11C). Inoculation with the 66.1 cells significantly increased the expression of MasR in the femur extrudate at both ~50 kDa and ~40 kDa (p<0.001 compared to sham group), while sham surgery did not significantly alter the expression of MasR in the femur extrudate as compared to the naïve animal group (FIG. 11D).

Repeated Dosing of Ang-(1-7) does not Alter Tumor Burden of Mice with Established CIBP or Alter Cell Viability In Vitro.

Figure 12B:
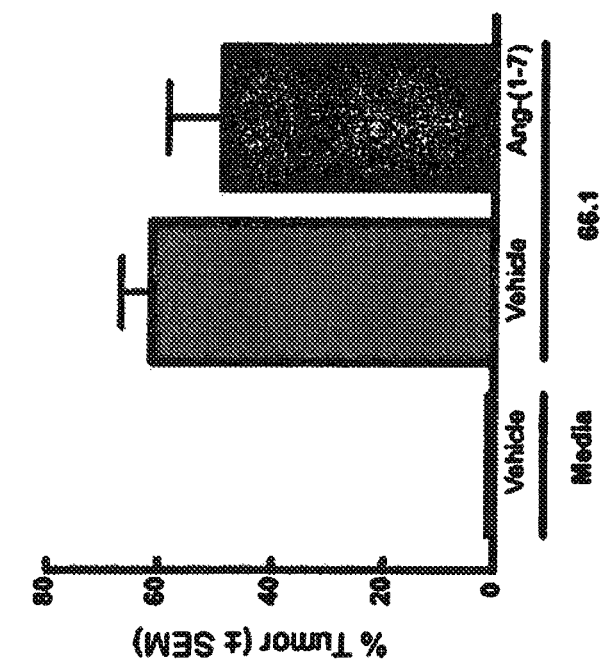
FIG. 12B is a bar graph showing the quantification of tumor tissue in the experimental animal femurs.
Figure 12A:
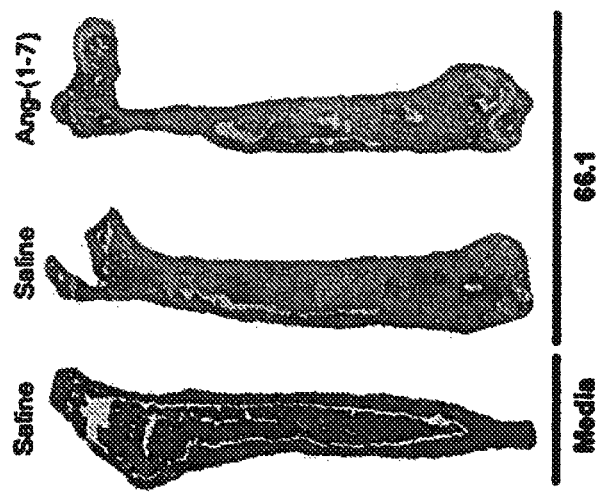
FIG. 12A is a series of photomicrograph of experimental animal femurs following various treatment regimens.
Figure 14:
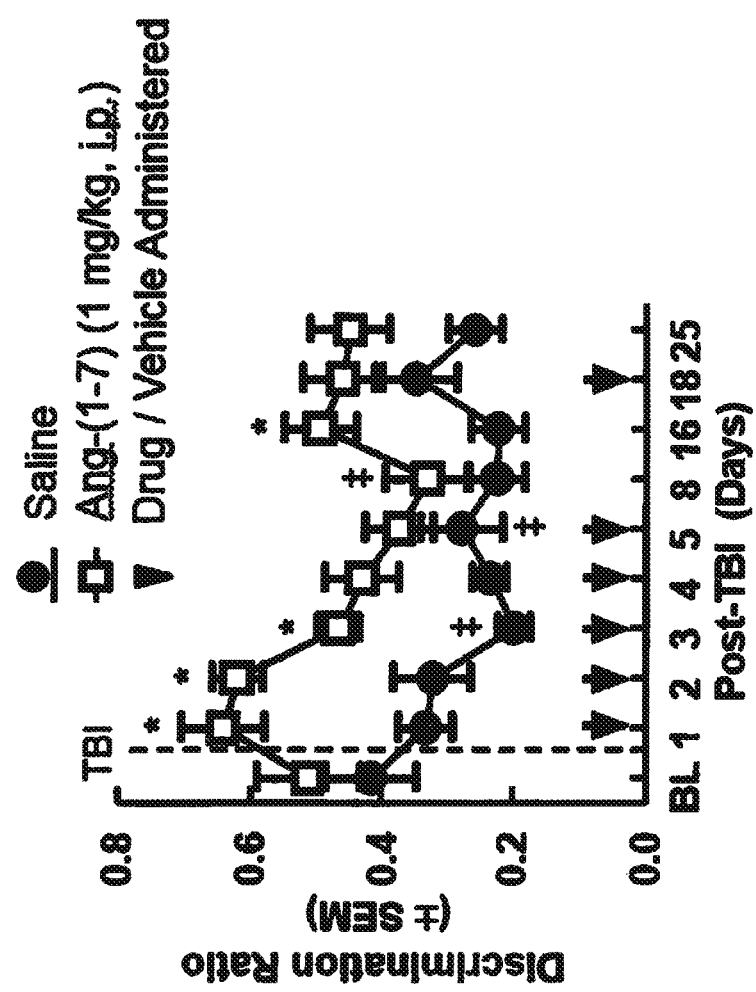
FIG. 14 is a line graph showing the discrimination ratio of experimental animals in a novel object recognition test after an acute traumatic brain injury (TBI).

Tumor burden was evaluated to determine whether the antinociceptive effect of repeated Ang-(1-7) administration results from an antineoplastic activity. Following chronic administration studies, femurs were harvested from animals, decalcified, and embedded in paraffin blocks prior to sectioning (5 micron) and hemotoxylin/eosin staining (FIG. 12A). The region of the bone containing cancer cells was quantified as a measure of total intramedullary content and represented as a percent of the entire cells within the bone. Repeated Ang-(1-7) administration did not significantly increase nor decrease the percent tumor of the bone (p=0.3, n=3-5) as compared to the saline-treated group (FIG. 12B). Thus, repeated Ang-(1-7) administration did not significantly impact tumor burden within the femur making it unlikely that the antinociceptive effect is secondary to an antineoplastic activity.

To verify in vivo findings, the effect of Ang-(1-7) on 66.1 cell viability was assessed in vitro. 66.1 cells were treated with vehicle, or increasing concentrations of Ang-(1-7) (1, 10, 100, or 1000 ng) for 24 hr and an XTT cell viability assay was performed. As compared to vehicle treated cells (relative absorbance (RA±SD)=1.02±0.09), each of the four Ang-(1-7) treatments did not significantly change cell viability (1 ng: 0.93±0.11; 10 ng: 0.93±0.07; 100 ng: 0.78±0.11, 1000 ng: 0.93±0.13). Together, these data indicate that Ang-(1-7) at the doses/concentrations tested neither promotes tumor cell proliferation nor causes tumor cell death both in vivo and in vitro.

Repeated Dosing of Ang-(1-7) does not Affect Bone Remodeling of Mice with Established CIBP.

Radiographic images of all chronically treated animals were taken on day 0, 7, 10, and 14 post-surgery to determine whether repeated Ang-(1-7) administration affected bone remodeling in mice with established CIBP (FIG. 13A). Day 14 images were scored by three blinded observers with the following scale: 0—healthy bone, 1—1-3 lesions; 2—4-6 lesions; 3—unicortical fracture; 4—bicortical fractures (FIG. 13B). A healthy bone was defined as one without any visible lesions or fractures, and a lesion was defined as a dark hole-like spot below the epiphyseal plate. While no animals experienced bicortical fractures, both saline and Ang-(1-7)-treated cancer-inoculated animals experienced unicortical fractures. Sham-treated (media) animals (7 out of 16) received scores of 0. As another marker of bone remodeling, levels of carboxy-terminal collagen crosslinks (CTX) in the serum were quantified (FIG. 13C). While cancer-inoculation significantly increased (p<0.05, n=3-4) CTX levels in the bone compared to both media controls, Ang-(1-7) repeated administration did not significantly alter CTX levels compared to the 66.1 saline treated group. Overall, daily Ang-(1-7) administration in mice with established CIBP did not significantly influence bone remodeling of the ipsilateral femur.

Example 5

Ang(1-7) Mitigates Cognitive Deficits Caused by Traumatic Brain Injury

Twenty-four C57/Bl6 mice (5.5 weeks, mass=18 to 20 g) were used for the duration of the study. The animals were housed in a humidity- and temperature-controlled environment and maintained on a 12:12 light:dark cycle (7:00 am-7:00 pm). Standard food and water were available ad libitum. The mice were divided into two main treatment groups: 1.) intraperitoneal (i.p.) injections of a normal saline (0.90%) vehicle (n=12) and (2.) i.p. injections of 0.1 mg/mL Ang-(1-7) (1 mg/kg) (n=12). A traumatic brain injury (TBI) model of closed head injury in mice using a pneumatic impactor capable of delivering a blow of a predetermined velocity, depth, and dwell time (duration of cortical depression) to a defined, 7.07 mm$^2$ area of the skull (Xiong, Mahmood, & Chopp, 2013) was used. Mice were first anesthetized using a 5% isoflurane vapor for induction. Once a response to toe-pinch was no longer observed, the mice were secured in the ear bars of a stereotaxic frame beneath the head impactor (TBI-0310 Impactor, Precision Systems) during which time 2.5% isoflurane was administered for maintenance of anesthesia. The parameters of each administered impact were set to the following: diameter of tip of cylindrical piston=3 mm; velocity of piston ($v_p$)=4.0 m/s; depth of impact ($d_i$)=1 mm; dwell time ($t_{dwell}$)=0.5 s. The point of impact was universalized in the medio-lateral plane to 1.5 mm left of the sagittal suture (as estimated by the mid-sagittal line of the mouse's head), and in the antero-posterior plane to an imaginary line intersecting the anterior point of insertion of the mouse's ears (approximately 1-2 mm anterior to the lambdoid suture). This point was chosen so as to avoid rupture of the superior sagittal sinus and the confluence of sinuses.

Immediately after being subjected to impact, mice were monitored for recovery of spontaneous respiration. Once noted to be breathing normally, mice were placed on the bedding of their normal enclosures and allowed to recover for 24 hours prior to their first, post-TBI novel object recognition trial.

The novel object recognition (NOR) task, as it pertains to the study of working memory and attention, is predicated on rodent preference of novel stimuli, whether spatial or otherwise (Ennaceur, Cavoy, Costa, & Delacour, 1989; Ennaceur & Delacour, 1988; Goulart et al., 2010; Silvers, Harrod, Mactutus, & Booze, 2007). When novel objects are paired simultaneously with familiar ones in an environment to which the animal has been habituated, it is possible to use the difference in exploration times of each object to make determinations of the degree of cognitive impairment relative to a measured baseline (Aggleton, Albasser, Aggleton, Poirier, & Pearce, 2010; Antunes & Biala, 2012; Olarte-Sanchez, Amin, Warburton, & Aggleton, 2015). The primary metric used to compare mice of different groups is the discrimination ratio (DR)—a value calculated as the ratio of time spent exploring the novel object (NO) to the total time spent exploring the familiar objects (FO) in addition the NO, i.e. DR=Time at NO/(Time at NO+Time at FO). In slight contrast to definitions of exploration used by previous authors (Aggleton et al., 2010; Aubele, Kaufman, Montalmant, & Kritzer, 2008; Ennaceur & Delacour, 1988; Goulart et al., 2010; Silvers et al., 2007), exploration in this investigation was defined as the directing of the nose toward an object at a distance of <2 cm from the object, touching an object with the nose or mouth, touching the object with both front paws, or standing on the object itself.

The overall structure of the NOR task, including associated familiarization trials, is as follows: mice from both groups underwent a two-day, combined habituation/familiarization phase, wherein they were allowed to roam freely in an evenly-lit, plastic, rectangular enclosure with walls 19.05 cm in height, containing three identical objects made of either glass or plastic, for five minutes. On the third day, the same test was run, but with one of the three "familiar" objects replaced with the NO, all spatial characteristics of the enclosure and objects therein remaining the same. Data collected on the third day constituted each mouse's baseline DR. On the fourth day, mice in both groups were subject to TBI as delineated in the previous section. The fifth day constituted the 24-hour post-TBI time point, wherein mice were administered an i.p. injection of either normal saline (vehicle group) or Ang-(1-7) solution (drug group) 30 minutes prior to undergoing the NOR task (NOs were rotated such that no animal saw the same NO twice). This pattern of injection and subsequent NOR trial was repeated to five days post-TBI. Both groups were run through two additional NOR tasks on post-TBI days 8 and 16 without prior drug or saline administration, again on post-TBI day 18 with prior drug or saline administration, and again on post-TBI day 25 without prior drug or saline administration. All NOR trials were filmed in high definition and manually reviewed using two stopwatches to determine the time spent at either a novel or familiar object.

Temporal data collected from each NOR trial was tabulated in a Microsoft Excel (2016) spreadsheet and individual discrimination ratio values calculated therein. Two-way ANOVA followed by a Tukey range test was performed using GraphPad Prism version 7.00 for Windows, GraphPad Software, La Jolla Calif. USA.

Example 6

Glycosylation of Ang(1-7) and its Derivatives Improves Pharmacokinetic Properties One known limitation of therapeutically administering native Ang(1-7) is its relatively short half-life and relatively poor blood-brain-barrier permeability. The following experiments used a rational drug design approach to assess the effect of adding various glycosides to Ang(1-7) and its derivatives on serum half-life and BBB permeability. Stability in vivo is affected by a number of factors, including susceptibility to peptidases and glycosidases, as well as aggregation phenomena in solution, and a wide array of binding events, including membrane absorption. Interaction of the glycopeptide drug with biological membranes is greatly influenced by both the geometry and degree of glycosylation. Our previous experience with glycopeptide GPCR agonists of a similar size indicates that the degree of glycosylation (mono- vs disaccharide) will not greatly affect interaction with the MAS receptor or its activation.

Figure 15A:
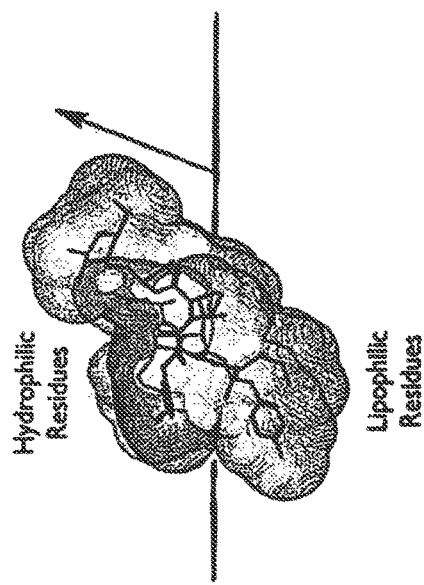
FIG. 15A is model of the three-dimensional structure of native Ang(1-7).

Membrane-bound conformations of the Ang(1-7)-based glycopeptides were modeled in silico by $^1$H-NMR NOESY measurements in the presence of $d_{25}$-SDS micelles. Using derived H—H distance constraints, a highly amphipathic folded structure was characterized. As illustrated in FIG. 15A, a Solvent Accessible Surface Area was constructed using the MOE® software package with the AMBER-99 force field to illustrate the resulting amphipathicity of the U-shaped folded structure. The uncharged lipophilic residues Val-Tyr-Ile are at the bottom of the "U" and insert into the membrane while charged "ends" protrude into the aqueous compartment. The "amphipathic moment" is suggested by the arrow.

Figure 15B:
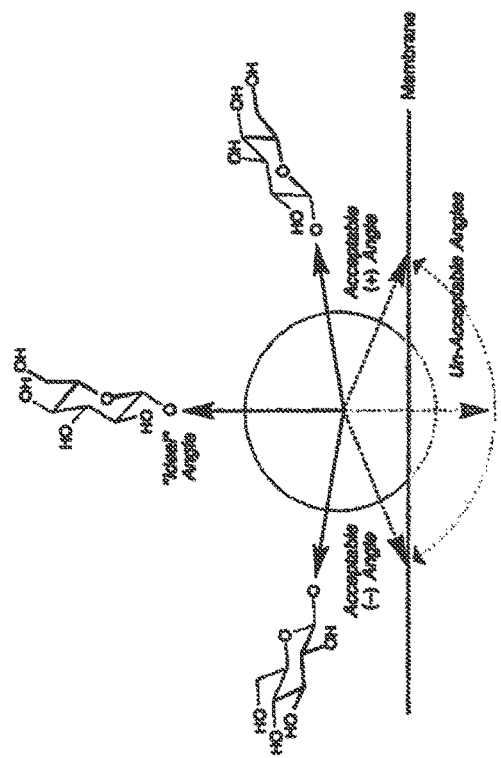
FIG. 15B is a computational model of various glycosylated Ang(1-7) derivatives.

FIG. 15B illustrates the MOE® calculations indicating that the linkage geometries of the saccharide and peptide chain can modify interactions of the resulting amphipathic glycopeptide with biological membranes prior to "docking" with the Mas receptor. D- or L-Serine, D- or L-Threonine, and D- or L-allo-Threonine, as well as D- or L-Cysteine orient the glycoside at different angles relative to the surface of the membrane.

Figure 16:
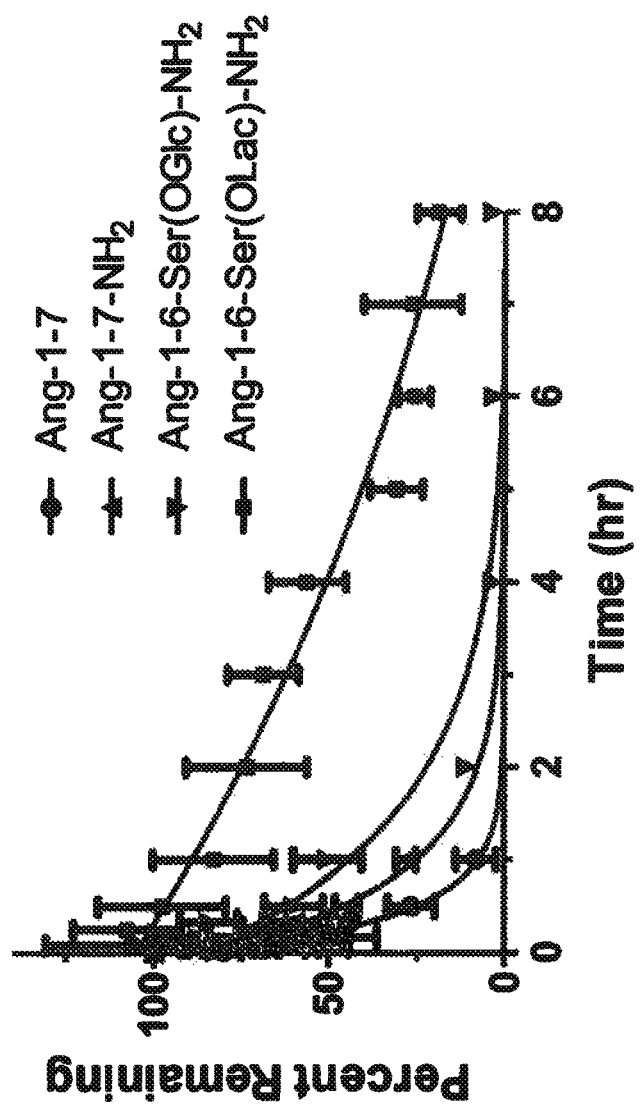
FIG. 16 is a line graph showing the in vitro serum half-life of native Ang(1-7) and various derivatives.

Based on these calculations, native Ang(1-7), Ang(1-7) having a C-terminal amino group (Ang 1-7-NH$_2$; SEQ ID NO: 2; "PN-A2"), PN-A5 (Ang 1-6-Ser(OGlc)-NH$_2$; SEQ ID NO: 10), and Ang 1-6-Ser(OLac)-NH$_2$ (i.e., PN-A5 in which lactose is substituted for the C-terminal glucose moiety) were produced and the serum half-life tested. Serum half-life was assessed by incubating 100 µM of each peptide in mouse serum for eight hours. Aliquots were withdrawn at the indicated time intervals and the peptide concentration was determined using HPLC-MS and expressed as a percentage of the initial concentration. As illustrated in FIG. 16 and Table 2, glycosylation significantly improved the serum half-life of the Ang(1-7) derivatives.

TABLE 2

In Vitro Serum Half-Life Assay

| Peptide | Half-life |
| --- | --- |
| Native Ang(1-7) | 14 min |
| Ang 1-7-NH$_2$ (PN-A2) | 21 min |
| Ang 1-6-Ser(OGlc)-NH$_2$ (PN-A5) | 1 hour |
| Ang 1-6-Ser(OLac)-NH$_2$ | 5.8 hours |

Figure 17A:
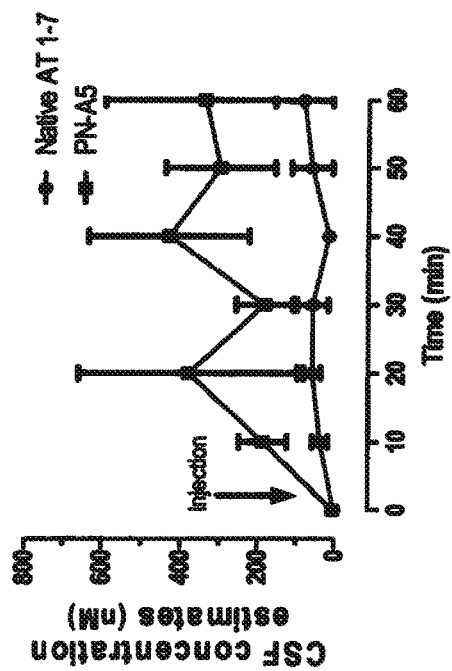
FIG. 17 is a series of line graphs showing the serum (FIG. 17A) and CSF (FIG. 17B) concentration of native Ang(1-7) and PN-A5.
Figure 17B:
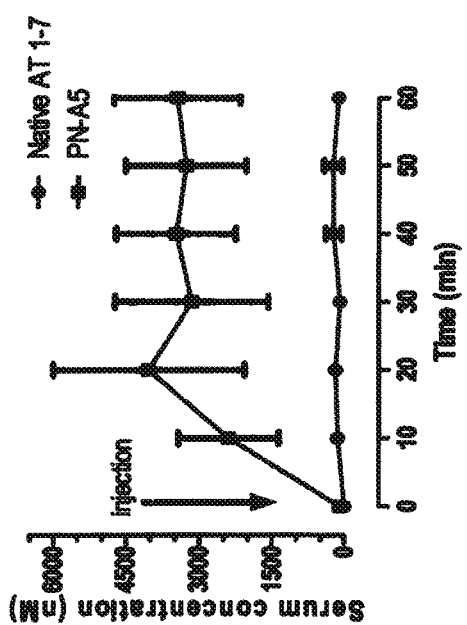

Based on these findings, the in vivo serum stability and BBB penetration was assessed in vivo for Ang(1-7) and PN-A5. The peptides (10 mg/kg) or vehicle control were individually subcutaneously injected into naïve mice. Serum concentrations were determined every 10 minutes by HPLC-MS using a 20-30 µl blood sample. Ang(1-7) and PN-A5 were found to reach a maximum serum concentrations of about 200 nM and about 3,500 nM, respectively (FIG. 17A). CSF samples were simultaneously withdrawn from the same animals via a microdialysis probe and assayed for the peptide concentration and corrected for basal CSF levels. Ang(1-7) and PN-A5 were found to reach a maximum CSF concentrations of about 50 nM and about 400 nM, respectively (FIG. 17B).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for providing analgesia to a subject having a painful condition comprising administering to the subject a therapeutically effective amount of an oligopeptide comprising an amino acid sequence consisting of the formula: $A^1$-$A^2$-$A^3$-$A^4$-$A^5$-$A^6$-$A^7$-$A^8$ (SEQ ID NO: 1) wherein
 - $A^1$ is selected from the group consisting of aspartic acid, glutamic acid, and glycosylated forms thereof;
 - $A^2$ is selected from the group consisting of arginine, lysine, and glycosylated forms thereof;
 - $A^3$ is selected from the group consisting of valine, alanine, isoleucine, leucine, and glycosylated forms thereof;
 - $A^4$ is selected from the group consisting of tyrosine, phenylalanine, tryptophan, and glycosylated forms thereof;
 - $A^5$ is selected from the group consisting of isoleucine, valine, alanine, leucine, and glycosylated forms thereof;
 - $A^6$ is selected from the group consisting of histidine, arginine, lysine, and glycosylated forms thereof;
 - $A^7$ is serine or a glycosylated form[s] thereof; and
 - $A^8$ is absent.

2. The method of claim 1, wherein the painful condition is selected from the group consisting of cancer-induced bone pain caused by either a primary or metastatic tumor, post-surgical pain, post-herpetic neuralgia, fibromyalgia, inflammatory pain, stroke-induced pain, trauma-based neuropathic pain, multiple sclerosis-induced pain, rheumatoid arthritis, and complex regional pain syndrome.

3. The method of claim 1, wherein the painful condition is cancer-induced bone pain.

4. The method of claim 1, wherein at least one of $A^1$-$A^8$ is glycosylated with a monosaccharide or disaccharide.

5. The method of claim 4, wherein at least one of the monosaccharides or disaccharides is selected from the group consisting of glucose, galactose, xylose, fucose, rhamnose, lactose, cellobiose, and melibiose.

6. The method of claim 1, wherein $A^7$ is glycosylated.

7. The method of claim 6, wherein $A^7$ is glycosylated with a saccharide selected from the group consisting of glucose, galactose, xylose, fucose, rhamnose, lactose, cellobiose, and melibiose.

8. The method of claim 1, wherein $A^7$ is terminated with an amino group.

9. The method of claim 7, wherein $A^7$ is terminated with an amino group.

10. The method of claim 1, wherein the oligopeptide is Ang 1-6-Ser(OG1c)-$NH_2$ SEQ ID NO: 10).

11. The method of claim 1, wherein the oligopeptide is Ang 1-6-Ser(OLac)-$NH_2$.

12. A method for providing analgesia to a subject having a painful condition comprising administering to the subject a therapeutically effective amount of an oligopeptide comprising an amino acid sequence consisting of the formula.: $A^1$-$A^2$-$A^3$-$A^4$-$A^5$-$A^6$-$A^7$-$A^8$ (SEQ ID NO:1) wherein
 - $A^1$ is selected from the group consisting of aspartic acid, glutamic acid, and glycosylated forms thereof;
 - $A^2$ is selected from the group consisting of arginine, lysine, and glycosylated forms thereof;
 - $A^3$ is selected from the group consisting of valine, alanine, isoleucine, leucine, and glycosylated forms thereof;
 - $A^4$ is selected from the group consisting of tyrosine, phenylalanine, tryptophan, and glycosylated forms thereof;
 - $A^5$ is selected from the group consisting of isoleucine, valine, alanine, leucine, and glycosylated forms thereof;
 - $A^6$ is selected from the group consisting of histidine, arginine, lysine, and glycosylated forms thereof;
 - $A^7$ is selected from the group consisting of proline, glycine, and glycosylated forms thereof; and
 - $A^8$ is serine or a glycosylated form thereof.

13. The method of claim 12, wherein the painful condition is selected from the group consisting of cancer-induced bone pain caused by either a primary or metastatic tumor, post-surgical pain, post herpatic neuralgia, fibromyalgia, inflammatory pain, stroke-induced pain, trauma-based neuropathic pain, multiple sclerosis-induced pain, rheumatoid arthritis, and complex regional pain syndrome.

14. The method of claim 12, wherein the painful condition is cancer-induced bone pain.

15. The method of claim 12, wherein at least one of $A^1$-$A^8$ is glycosylated with a monosaccharide or disaccharide.

16. The method of claim 15, wherein at least one of the monosaccharides or disaccharides is selected from the group consisting of glucose, galactose, xylose, fucose, rhamnose, lactose, cellobiose, and melibiose.

17. The method of claim 12, wherein $A^8$ is glycosylated.

18. The method of claim 17, wherein $A^8$ is glycosylated with a saccharide selected from the group consisting of glucose, galactose, xylose, fucose, rhamnose, lactose, cellobiose, and melibiose.

19. The method of claim 12, wherein $A^8$ is terminated with an amino group.

20. The method of claim 18, wherein $A^8$ is terminated with an amino group.

21. The method of claim 12, wherein the oligopeptide is selected from the group consisting of Ang 1-7-Ser-$NH_2$ (SEQ ID NO: 7), Ang 1-7-Ser(OG1c)-$NH_2$ (SEQ ID NO: 8), and Ang 1-6-Ser(OLac)-$NH_2$ (SEQ ID NO: 9).

* * * * *

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Glu, Ala or a derivative thereof
<220> FEATURE:
<221> NAME/KEY: MOD_RES
<222> LOCATION: (2)..(2)
<223> OTHER INFORMATION: Arg, His, Lys or a derivative thereof
<220> FEATURE:
<221> NAME/KEY: MOD_RES
<222> LOCATION: (3)..(3)
<223> OTHER INFORMATION: Val, Ala, Ile, Leu or a derivative thereof
<220> FEATURE:
<221> NAME/KEY: MOD_RES
<222> LOCATION: (4)..(4)
<223> OTHER INFORMATION: Tyr, Phe, Trp or a derivative thereof
<220> FEATURE:
<221> NAME/KEY: MOD_RES
<222> LOCATION: (5)..(5)
<223> OTHER INFORMATION: Ile, Val, Ala, Leu or a derivative thereof
<220> FEATURE:
<221> NAME/KEY: MOD_RES
<222> LOCATION: (6)..(6)
```

```
<223> OTHER INFORMATION: His, Arg, Lys or a derivative thereof
<220> FEATURE:
<221> NAME/KEY: MOD_RES
<222> LOCATION: (7)..(7)
<223> OTHER INFORMATION: Pro, Gly, Ser or a derivative thereof
<220> FEATURE:
<221> NAME/KEY: MOD_RES
<222> LOCATION: (8)..(8)
<223> OTHER INFORMATION: Ser, Thr, hydroxyproline, a derivative thereof
      or absent

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Homo sapiens

<400> SEQUENCE: 2

Asp Arg Val Tyr Ile His Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: D-amino acid

<400> SEQUENCE: 3

Pro His Ile Tyr Val Arg Asp
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro His Ile Tyr Val Arg Asp
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: D-amino acid

<400> SEQUENCE: 5

Asp Arg Val Tyr Ile His Pro
1               5

<210> SEQ ID NO 6
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term -NH2

<400> SEQUENCE: 6

Asp Arg Val Tyr Ile His Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term -NH2

<400> SEQUENCE: 7

Asp Arg Val Tyr Ile His Pro Ser
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Glucosylated-Ser
<220> FEATURE:
<223> OTHER INFORMATION: C-term -NH2

<400> SEQUENCE: 8

Asp Arg Val Tyr Ile His Pro Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lactosylated-Ser
<220> FEATURE:
<223> OTHER INFORMATION: C-term -NH2

<400> SEQUENCE: 9

Asp Arg Val Tyr Ile His Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (7)..(7)
<223> OTHER INFORMATION: Glucosylated-Ser
<220> FEATURE:
<223> OTHER INFORMATION: C-term -NH2

<400> SEQUENCE: 10

Asp Arg Val Tyr Ile His Ser
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Ser, Glucosylated-Ser, or Lactosylated-Ser
<220> FEATURE:
<223> OTHER INFORMATION: C-term -NH2

<400> SEQUENCE: 11

Ala Xaa Xaa Tyr Ile Xaa Pro Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Ser, Glucosylated-Ser, or Lactosylated-Ser
<220> FEATURE:
<223> OTHER INFORMATION: C-term -NH2

<400> SEQUENCE: 12

Asp Arg Xaa Tyr Xaa His Pro Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
```

```
<220> FEATURE:
<221> NAME/KEY: MOD_RES
<222> LOCATION: (8)..(8)
<223> OTHER INFORMATION: Ser, Glucosylated-Ser, or Lactosylated-Ser
<220> FEATURE:
<223> OTHER INFORMATION: C-term -NH2

<400> SEQUENCE: 13

Asp Arg Xaa Xaa Xaa His Pro Ser
1               5
```